United States Patent [19]

Mizrakh et al.

[11] Patent Number: 6,160,008
[45] Date of Patent: Dec. 12, 2000

[54] PHARMACEUTICAL COMPOSITIONS COMPRISING S-ALKYLISOTHIOURONIUM DERIVATIVES

[75] Inventors: Lev Mizrakh, Rehovot, Israel; Valentin Znamensky, Moscow, Russian Federation; Evgeni Arzamastsev, Moscow, Russian Federation; Lev Shagalov, Moscow, Russian Federation; Valeri Kovtun, Moscow, Russian Federation; Vladimir Jashounsky, Moscow, Russian Federation; Marina Kochetkova, Moscow, Russian Federation; Galina Bondareva, Moscow, Russian Federation; Olga Terekhova, Moscow, Russian Federation; Victor Gikavy; Victor Darchuk, both of Kishinev, Rep. of Moldova

[73] Assignee: Meditor Pharmaceuticals Ltd., Rehovot, Israel

[21] Appl. No.: 09/269,405

[22] PCT Filed: Sep. 25, 1997

[86] PCT No.: PCT/IL97/00314

§ 371 Date: Jun. 9, 1999

§ 102(e) Date: Jun. 9, 1999

[87] PCT Pub. No.: WO98/13036

PCT Pub. Date: Apr. 2, 1998

[30] Foreign Application Priority Data

Sep. 26, 1996 [RU] Russian Federation ............. 96119163
Sep. 19, 1997 [RU] Russian Federation ............. 97115433

[51] Int. Cl.[7] ........................ A61K 31/21; A61K 31/155; A61P 9/02; A61P 39/00
[52] U.S. Cl. ............................................................ 514/508
[58] Field of Search .................................................. 514/508

[56] References Cited

U.S. PATENT DOCUMENTS 3,116,327 12/1963 Kartinos .
3,123,636  3/1964 Loev et al. .
3,657,337  4/1972 Houlihan et al. .

OTHER PUBLICATIONS

Korstanje et al., "Influence of repsiratory acidosis o$_r$ $_a$lkalosis on pressor response medicated by a1–and a2 andrenceptors in pithed normotensive rats", *Arch. Pharmacol.*, vol. 330, pp. 187–192, (1985).
Zherebchenko et al., "Radioprotective Action of Salts of Isothiourea S–alkyl–Substit$_u$ted Derivative$_s$ in Separate and Combined Application Thereof", *Radiobiology*, vol. 8, pp. 582–587, (1968).
Atkinson et al., "Acidosis Induced by Catecholamines and Reduction of Cardiovascular Responses to Catecholamines in Acidosis", vol. 50, pp. 847,859, (1972).

Avakyan, "Adrenoreceptor function pharmacological regulation", *M. Medicine*, pp. 8–9, (1988).
Mashkovsky, Medicines, 12 ed., Moscow, Medicine, pp. 303, (1993).
Kulinsky et al., "Abstracts of Articles $_s$ored in the All–Union Research Institute for Technical Information" *Bulletin of Experimental Biological Medicine*, pp. 9, (1984).
Mukhin et al., "Hypertensive medicine", pp. 118–122, (1983).
Vromen et al., "Effects of S–isopropyl isothiourea, a potent inhibitor of nitric oxide synthase, in severe hemorrhagic shock", *J. Appl. Physiol.*, vol. 81, No. 2, pp. 707–715, (1996).
Squadrito et al., "Effects of S–ethylisothiorea, a potent inhibitor of nitric oxide synthase, alone or in combination with a nitric oxide donor in splanchnic artery occlusion shock", *Br. J. Pharmacol.*, vol. 114, No. 2 pp. 510–516, (1995).
Southan et al., "Isothiouresa: potent inhibitor of nitric oxide synthases with variable isoform selectivity" Br. J. Pharmacol., vol. 114, No. 2, pp. 510–516, (1995).
Mukhin et al., "Prevention of the provoking action of insulin on oxygen poisoning and preservation of specific properties of the drug under hyperbaric oxygenation", vol. 46, No. 4, pp. 96–99, (1983).
"Experimental justification for the application of some isothiuronium derivatives as radioprotectants", *Radiobiologiya*, vol. 21, No. 4, pp. 68, (1981).
"Effect of the prophylactic administration of the phosphorus–containing derivatives of S–alkylisothiuronium on the survival time of irradiated animals", *Izv. Estestvennonauchn. Inst. Permsk. Gos. Univ.*
"Local action of some isothiuronium derivatives used intramuscularly", *Deposited Doc.*, vol. 00 No. 6, pp. 1259–1260, (1969).
"Reaction of dialkyl phosphonates with thiourea", *ZH. Obshch. Khim.*, vol. 39, No. 6, pp. 1259–1260 (1969).
Chemical abstracts, vol. 70, No. 1, p. 59.
Chemical abstracts, vol. 93, No. 1, p. 28.
Database Embase, Elsevier Science Publishers, Amsterdam, NL, Dialog AN:5521869, EMBASE AN:84017535, Gikavyi, et al., "Effect of combined etiron and phentolamine on the systemic hemodynamics." vol. 46, No. 6, 1983, abstract.
Chemical Abstracts 57(1962): 16393d; Teichmann, H. J. Prakt. Chem. 16, 45–54 (1962).

*Primary Examiner*—Michael G. Ambrose
*Attorney, Agent, or Firm*—Browdy and Neimark

[57] ABSTRACT

S-Alkylisothiouronium salts with phosphorus-containing acids are described. The compounds are used in processes of treating acute hypotension, which may result, for example, from shock or hemorrhage, and in processes for treating hyperoxic conditions, for example, oxygen poisoning.

14 Claims, 13 Drawing Sheets

PHARMACEUTICAL COMPOSITIONS COMPRISING S-ALKYLISOTHIOURONIUM DERIVATIVES

FIELD OF THE INVENTION

The present invention relates to S-alkylisothiouronium salts with phosphorus-containing acids which affect arterial blood pressure and possess oxygen protective activity, and to the use of such compounds in cases of acute and chronic hypotension (hemorrhage, trauma, shock, poisoning), especially for first aid, as well as in cases of oxygen poisoning.

BACKGROUND OF THE INVENTION

Most medicaments affecting arterial blood pressure act either via the stimulation of alpha-adrenergic receptors or directly on the visceral muscles of the vascular wall. Adrenomimetics, e.g. adrenaline, noradrenaline, adrianol, phenylephrine (mezaton) ephedrine, ethylephrine, etc., and polypeptides, e.g. glucogon, angiotensin, octapressin, etc. are most often used.

Mezaton is a well known adrenomimetic drug (M. D. Mashkovsky, Medicines, 12-th edd., Moscow., Medicine, 1993, Part I, p. 303), having a pharmaceutical activity related to that of the compounds of the present invention. Mezaton (1-(m-hydroxyphenyl)-2-methylaminoethanol hydrochloride) selectively stimulates α1-adrenoreceptors, causes arterial constriction and increase in systolic and diastolic pressure (with possible reflectoral bradycardia). Mezaton practically does not have cardiostimulating effect. Unlike adrenaline and noradrenoline, mezaton is not a catecholamine (it contains only one hydroxyl group in aromatic nucleus) and is not influenced by the enzyme—catechole-O-methyltransferase, therefore it is more stable and has a prolonged effect. Mezaton's anti-hypotensive effect usually lasts for approximately 20 minutes after a single intravascular injection.

Adrenomimetics, among them mezaton, have some common shortcomings, as they increase tissue oxygen consumption, cause metabolic acidosis, may cause arrhythmia (especially during general anesthesia), and exert exciting influence on the central nervous system (O. M. Avakyan, Adrenoreceptor function pharmacological regulation, M., Medicine, 1988, p. 8; V. G. Kulinsky, A. N. Kovalevsky, Bulletin of Experimental Biological Medicine, 1984, p. 9). The appearance of secondary hypotension is characteristic of them. Adrenomimetics do not correct arterial hypotension caused by adrenergic blocking agents, and have only a slight anti-hypotensive effect in case of metabolic acidosis (C. Kortanje, V. I. Mathy, R. Charldorp, Haunyn-Gchinedeleg in *Arch. Pharmacol.*, 330:3, 187–192 (1985)).

Medicaments with polypeptide structure have a short adrenomimetic effect. To achieve prolonged effect they are injected in the form of perfusion (I. M. Autkunson, S. I. Dusting, V. I. Rand, *Aust. J. Exp. Biol. Med.*, 50:847–859 (1972)).

In the pathogenesis of oxygen poisoning, the main function belongs to the adrenoreceptors $\beta_1$ and $\beta_2$ which affect the metabolism of catecholamines. A known compound used in hyperoxia experiments on animals is etyron (S-ethylisothiouronium bromide). Etyron was described in the literature (E. A. Mukhin et al., Hypertensive medicines 1983, 118–122) as having a protective activity under increased oxygen pressure.

S-Alkylisothiouronium salts with phosphorus containing acids, among them Difetur (S-ethylisothiouronium diethylphosphate) are described in the art as having distinct radioprotective effect and their toxicological characteristics have been studied (P. G. Zherebchenko, Yu. D. Zilber, G. P. Pospekhov, et al., *Radiobiologya*, 8:582–587 (1968); Zh. A. Goloschapova, T. N. Tuzhilkova, L. I. Mizrakh, *Radiobiology*, 21:521–525 (1981)).

OBJECT OF THE INVENTION

The object of the present invention is to provide new medicaments having an effect of increasing arterial blood pressure. In addition, it is the object of the present invention to provide a new medicament having oxygen protective effect.

SUMMARY OF THE INVENTION

The above object is achieved by the use of S-alkylisothiouronium salts with phosphorus containing acids of formula I:

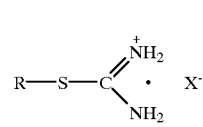

I wherein R is a straight or branched alkyl, optionally substituted by halogen, and X is an anion derived from a phosphorus containing acid, for the preparation of a medicament for increasing arterial blood pressure or for protection against hyperoxia.

Phosphorus containing salts of S-alkylisothiouronium may be prepared by known methods, for example by alkylating thiourea with appropriate trialkylphosphates or dialkylphosphites while heating in an organic solvent.

In another aspect, the invention relates to pharmaceutical compositions for increasing arterial blood pressure or for protection against hyperoxia, comprising an effective amount of a compound of formula I.

Still, further provided by the present invention, is a method of increasing arterial blood pressure, or for protection in hyperoxic conditions, by administering to a mammal in need of such treatment a therapeutically effective amount of a compound of formula I.

In a further aspect, the invention relates to some new S-alkylisothiouronium derivatives, namely: S-methylisothiouronium dimethylphosphate and S-isobutylisothiouronium isobutylphosphite. Also provided by the present invention are novel pharmaceutical compositions comprising, as active ingredient, at least one of these new compounds.

The term "alkyl" means a saturated hydrocarbon chain containing 1 to 12, preferably 1 to 6 carbon atoms, such as methyl, ethyl, n-propyl, isopropyl, n-butyl, tert-butyl, n-pentyl, n-hexyl and the like. The alkyl may also contain halogen atoms.

The compound of formula I may be used for the treatment of a number of diseases or disorders associated with or resulting from hypotension (decrease in blood pressure) or hyperoxia (excess of oxygen in the system). The treatment may be administered to a subject (which may be a human, as well as a non-human animal) by:

(i) preventing the disease or disorder, that is, causing the clinical symptoms of the disease not to develop;

(ii) inhibiting the disease, that is, arresting the development of clinical symptoms; and/or (iii) relieving the disease, that is, causing the regression of clinical symptoms.

The term "effective amount" means a dosage sufficient to impart a therapeutic effect. This will vary depending on the dosage form, the age group of the patient, the severity of the disease, as well as on various other factors as known per se.

DETAILED DESCRIPTION OF THE INVENTION

A preferred compound for use in accordance with the invention is S-ethylisothiouronium diethylphosphate (Difetur) which was shown in the experiments described below as being the most active compound (Tables 2–5, FIGS. 11–13). This compound does not influence negatively the acid-base balance (Tables 6, 7), does not cause secondary hypotension (FIGS. 11–13), retain its activity in conditions of alpha-adrenergic blockade (Table 3), practically does not lose efficiency in case of metabolic acidosis (Table 4), and improves system hemodynamic indices in hemorrhagic shock conditions (Table 4). In addition, Difetur was found to exceed Etyron in oxygen protective activity (Tables 15 and 16), to improve blood serum biochemical indices (Table 17) and to efficiently protect lungs from the toxic effect of increased oxygen pressure (Table 18).

It was found that S-ethylisothiouronium diethylphosphate affects systemic hemodynamic indices in the following way: the peripheral vascular resistance increases, the stroke volume and central blood volume increase, and the work of the left ventricle improves (Table 4).

In case of shock conditions (traumatic, hemorrhagic) intramuscular injection S-ethylisothiouronium diethylphosphate enables medical relief on a pre-hospital stage (Table 4) which is unattainable with the medicines currently used.

S-ethylisothiouronium diethylphosphate is described in the literature as having radioprotective effect (Radiobiology, 21:521–525 (1981). However, according to the present invention, as demonstrated in the biological tests shown below, S-ethylisothiouronium diethylphosphate was found to have new activities, and can thus be used as a medicament for increasing arterial blood pressure in cases of acute arterial hypotension due to surgical interference, trauma, poisoning, shock condition, hemorrhages; in conjunction with epidural anesthesia; in overdose of ganglion blockers (Table 5), alpha-adrenergic blockers (Table 3), neuroleptics, anesthetics; and in other conditions when adrenomimetics are contra-indicated or ineffective (Tables 6, 7). Difetur was also found to possess oxygen protective activity and, thus, can be used as a medicament for protecting against oxygen poisoning conditions caused by hyperoxia.

Figure 12:
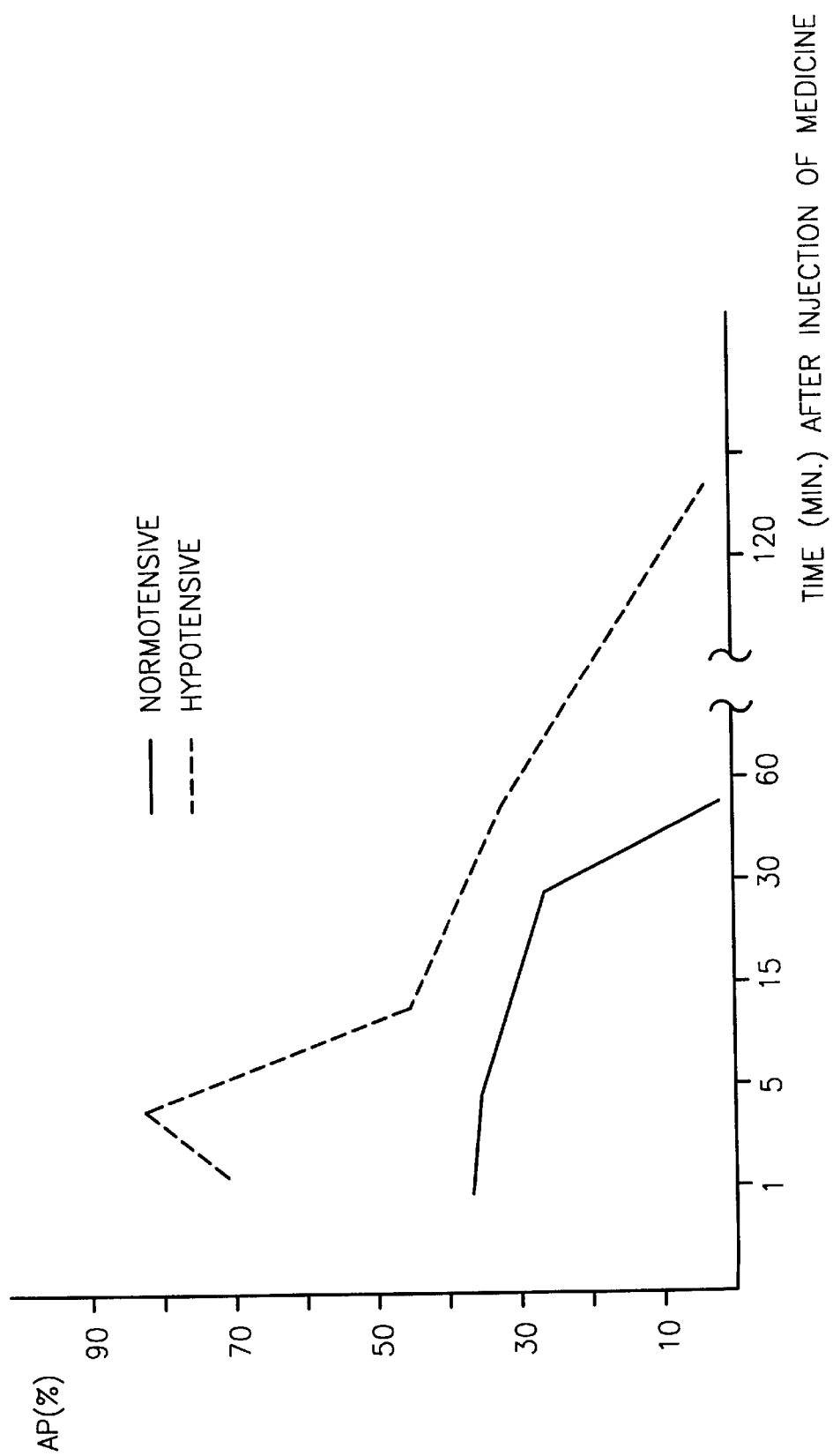
FIG. 12 shows the changes in arterial blood pressure (percent increase relative to the initial value) in dogs after a single intravenous S-ethylisothiouronium diethylphosphate injection at a dose of 5 mg/kg.
Figure 13:
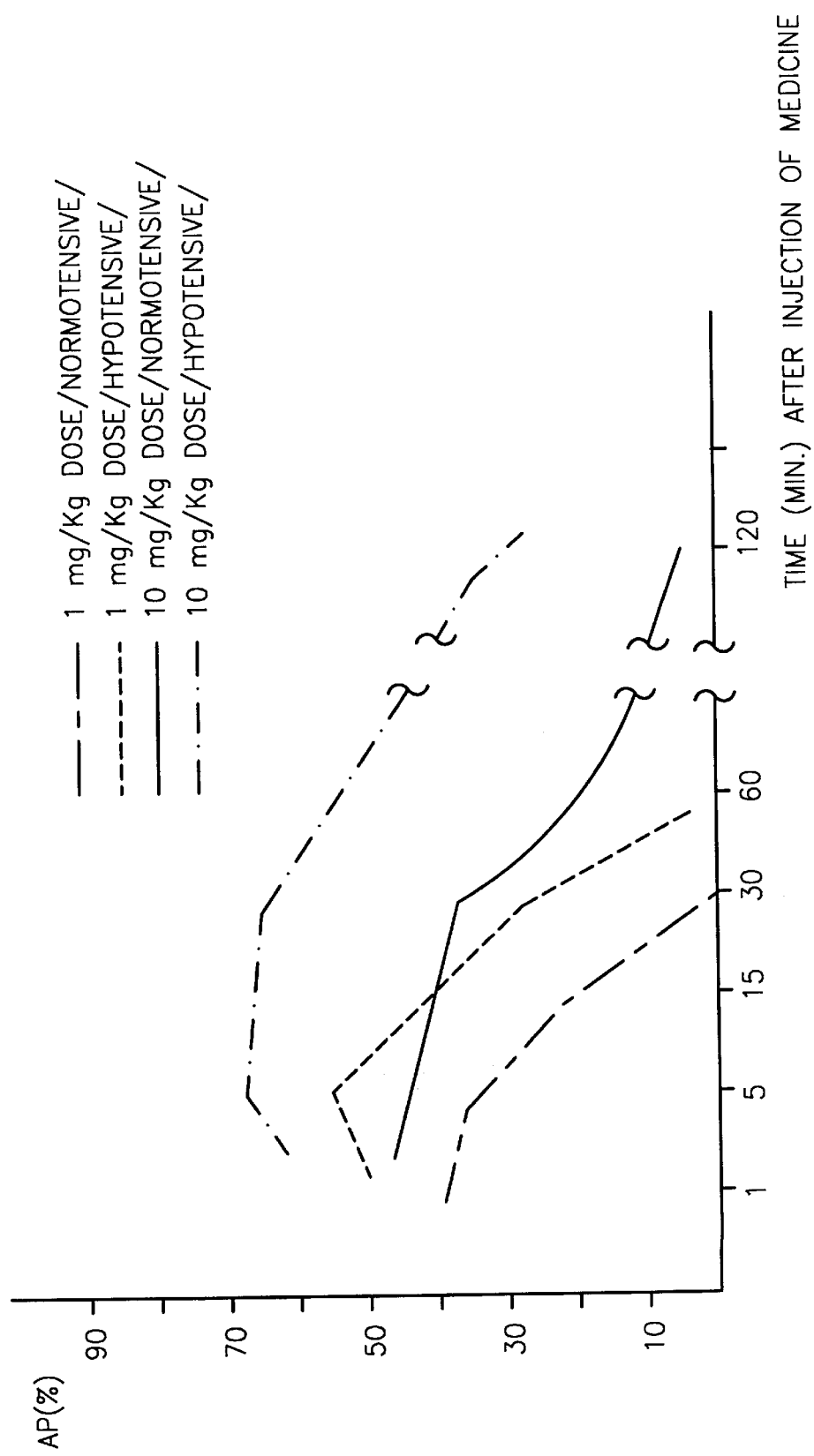
FIG. 13 shows the influence of intravenous S-ethylisothiouronium diethylphosphate injection on hypotensive and normotensive dogs.

It is to be noted that the influence of S-ethylisothiouronium diethylphosphate is greater in hypotensive than in normotensive animals (FIGS. 12, 13).

Compounds of formula I create new possibilities for the treatment of acute and possibly chronic arterial hypotension as well as in cases of first aid of traumatized patients.

Phosphorus containing salts of S-alkylisothiouronium may be formulated in a variety of ways. Examples are capsules, tablets and injectable formulations for parenteral, e.g. intramuscular or intravenous injection. However, other forms may also be used, e.g. liquid oral formulations, suppositories. In emergency cases, parenteral injection of an injectable preparation containing 1%–10% (W/V) of the active ingredient may be employed. The dose for parenteral administration is typically 0.1–20 mg/kg of body mass, preferably 0.2–5 mg/kg. In solid dosage forms, a unit dosage of about 4 to about 400 mg of the active compound is typically employed.

Phosphorus containing derivatives of S-alkylisothiouronium have a low toxicity ($LD_{50}$ is 100–1000 mg/kg).

The invention will be illustrated below, with reference to some non limiting examples.

EXAMPLES

A. Synthesis of phosphorus containing salts of S-alkylisothiouronium

1. S-ethylisothiouronium diethylphosphate

A mixture of 36.6 g (0.2 M) triethyphosphate and 15.2 g (0.2 M) of ground thiourea was heated to 132–135° C. while stirring and kept at this temperature till thiourea completely dissolves (approximately 3–5 minutes). While the stirring was continued the heating was stopped, and the mixture let to cool. When the reaction mixture cooled to 50–60° C., 40 ml of acetone were added. Product crystallization began when the temperature was subsequently falling and completed within 3 hours. Crystals were filtered, washed with 10 ml of acetone, and dried to constant weight. 26.6 g of raw S-ethylisothiouronium diethylphosphate were isolated and recrystallized from acetone. 24.6 g (47.7% of theoretical amount) of S-ethylisothiouronium diethylphosphate were obtained, melting point 144–146° C. (According to literature data, the melting point is 145° C. (J. B. Parker, 1961)). Substance content—99.6%.

Elemental analysis found, %: C—32.57, H—7.43, N—10.75, P—11.87, S—12.47. $C_7H_{19}N_2O_4PS$. It was calculated, %: C—32.56, H—7.36, N—10.85, P—12.01, S—12.40.

2. S-isopropylisothiouronium isopropylphosphite

A mixture of 13.7 g (0.082 M) diisopropylphosphite and 6.2 g (0.082 M) of thiourea was heated to 135° C. in a three-neck flask equipped with a stirrer and a condenser with calcium chloride drying tube. Thiourea dissolved during heating and a homogenous mass found. The heating at this temperature was continued for 60–75 min. till the reaction mixture became slightly red. The mixture was cooled to 40–50° C. and 50 ml of acetone were poured to obtain, after 30 mins., 10 g (50.8%) of the desired product. After crystallization, 6 g of S-isopropylisothiouronium isopropylphosphite phosphite were obtained, melting point 169–171° C. According to literature data, the melting point is 164° C. (V. V. Orlovsky, B. A. Vovsy, Zh. Obsz. Khim., 39:1259–1260 (1969).

3. S-ethylisothiouronium metaphosphate

A mixture of 8.65 g (0.05 M) of diethylchlorophosphate and 3.8 gm (0.05 M) of ground thiourea was heated while stirring to 145° C., over a period of 1.5 hours: The reaction mixture was kept at this temperature for 10 minutes, it was cooled, a mixture of ethanol-acetone (3:2) was added, and left overnight. The precipitate was filtered, washed with ethanol-acetone and dried overnight. After crystallization from aqueous alcohol, 6.0 g (65%) of S-ethylisothiouronium metaphosphate were obtained, melting point 224–225° C.

Elemental analysis (%): C—19.57, H—4.90, P—16.73, S—17.32; $C_7H_{19}N_2O_4PS$. Calculated values (%): C—19.55, H—4.90, P—16.85, S—17.40.

This substance was also prepared by another method, as shown below.

A mixture of 4.25 g ethyl metaphosphate and 3.0 g of thiourea was heated while stirring to 145° C. within 1.5 hour, kept at this temperature during 10 minutes, then it was cooled, and treated as mentioned above. 5.0 g (69%) of S-ethylisothiouronium metaphosphate, melting point 223–224° C. was obtained.

The following compounds were prepared by the same procedure:

S-methylisothiouronium methylphosphite with a yield of 73%, melting point 119–120° C. According to literature data, melting point is 120° C. (V. V. Orlovsky, 1969);

S-methylisothiouronium dimethylphosphate, with a yield of 54%;

S-ethylisothiouronium ethylphosphite with a yield of 62%, melting point 109–110° C. According to literature data, melting point is 112° C. (V. V. Orlovsky, 1969);

S-propylisothiouronium propylphosphite with a yield of 40%, melting point 99–100° C. According to literature data melting point is 102° C. (V. V. Orlovsky, 1969);

S-isopropylisothiouronium metaphosphate, with a yield of 21%, melting point 257–259° C. According to literature data, melting point is 259° C.;

S-butylisothiouronium di-butylphosphate with a yield of 38%, melting point 96–98° C. According to literature data, melting point is 98° C. (V. V. Orlovsky, 1969);

S-isobutylisothiouronium isobutylphosphite with a yield of 43%, melting point 162–164° C.

The structure of the obtained compounds was confirmed by IR-spectra: all compounds had characteristic absorption bands in the region of $v_{PO}$ 1195–1207 cm$^{-1}$, $v_{CN}$ 1680–1695 cm$^{-1}$, $v_{NH}$ 1568–1590 cm$^{-1}$; and UV-spectra with characteristic absorption at $\lambda_{MAX}$—201–203 nm and 223–225 nm.

B. Biological study of the influence of S-alkylisothiouronium salts with phosphorus containing acids on arterial blood pressure Experiments were performed on 52 anesthetized (intraperitoneally with 45 mg/kg of sodium pentobarbital) cats of both genders with body mass of 2.8–4.2 kg. Arterial pressure was measured by a mercury pressure gauge; measurements were also performed by ECG. Simultaneously, the respiratory frequency was registered. The hypertensive effect was determined as percent increase relative to the initial level of systolic arterial pressure (SAP). The duration of observation was 1–3 hours; the heart rate (HR) was calculated on the basis of ECG. The obtained results are graphically shown in FIGS. 1–10 and summarized in Table 1.

TABLE 1

Influence of intravenous administration of phosphorus containing derivatives of S-alkylisothiouronium on the arterial blood pressure, cardiovascular system and respiratory frequency (in cats)

| Substance | Time to achieve maximum effect | Hypertensive activity, % | Duration of effect | Influence on HR | R R |
|---|---|---|---|---|---|
| S-methylisothiuronium methylphosphite, | 2 min | > SAP by 25 mm Hg (20.8%) | > 1 hour | No influence | Increases |
| S-methylisothiuronium dimethylphosphate, | 2 min | > SAP by 27.5 mm Hg (20.8%) | 1.5 hour | Bradycardia | Increases |
| S-ethylisothiuronium methylphosphate, | 2 min | > SAP by 25 mm Hg (14.8%) | up to 1 hour | Bradycardia | No influence |
| S-ethylisothiuronium ethylphosphite | 2 min | > SAP by 25 mm Hg (15.6%) | 1.5 hour | Bradycardia | No influence |
| S-ethylisothiuronium diethylphosphate | 2 min | > SAP by 40 mm Hg (40%) | 1–1.5 hour | Bradycardia | Increases |

TABLE 1-continued

Influence of intravenous administration of phosphorus containing derivatives of S-alkylisothiouronium on the arterial blood pressure, cardiovascular system and respiratory frequency (in cats)

| Substance | Time to achieve maximum effect | Hypertensive activity, % | Duration of effect | Influence on HR | R R |
|---|---|---|---|---|---|
| S-propylisothiuronium propylphosphite | 2 min | > SAP by 26.4 mm Hg (24.6%) | up to 1 hour | Moderate bradycardia | No influence |
| S-isopropylisothiuronium metaphosphate | 15 min | > SAP by 27 mm Hg (20.3%) | 2 hour | Bradycardia | Increases |
| S-isopropylisothiuronium isopropylphosphite | 2 min | > SAP by 40 mm Hg (28.8%) | 2 hour | Bradycardia | No influence |
| S-butylisothiuronium dibutylphosphate | 30 min | > SAP by 7 mm Hg (5.6%) | up to 1 hour | Moderate bradycardia | No influence |
| S-isobutylisothiuronium isobutylphosphate | 2 min | > SAP by 22.6 mm Hg (14.8%) | 2 hour | Moderate bradycardia | Increases |

Figure 1:
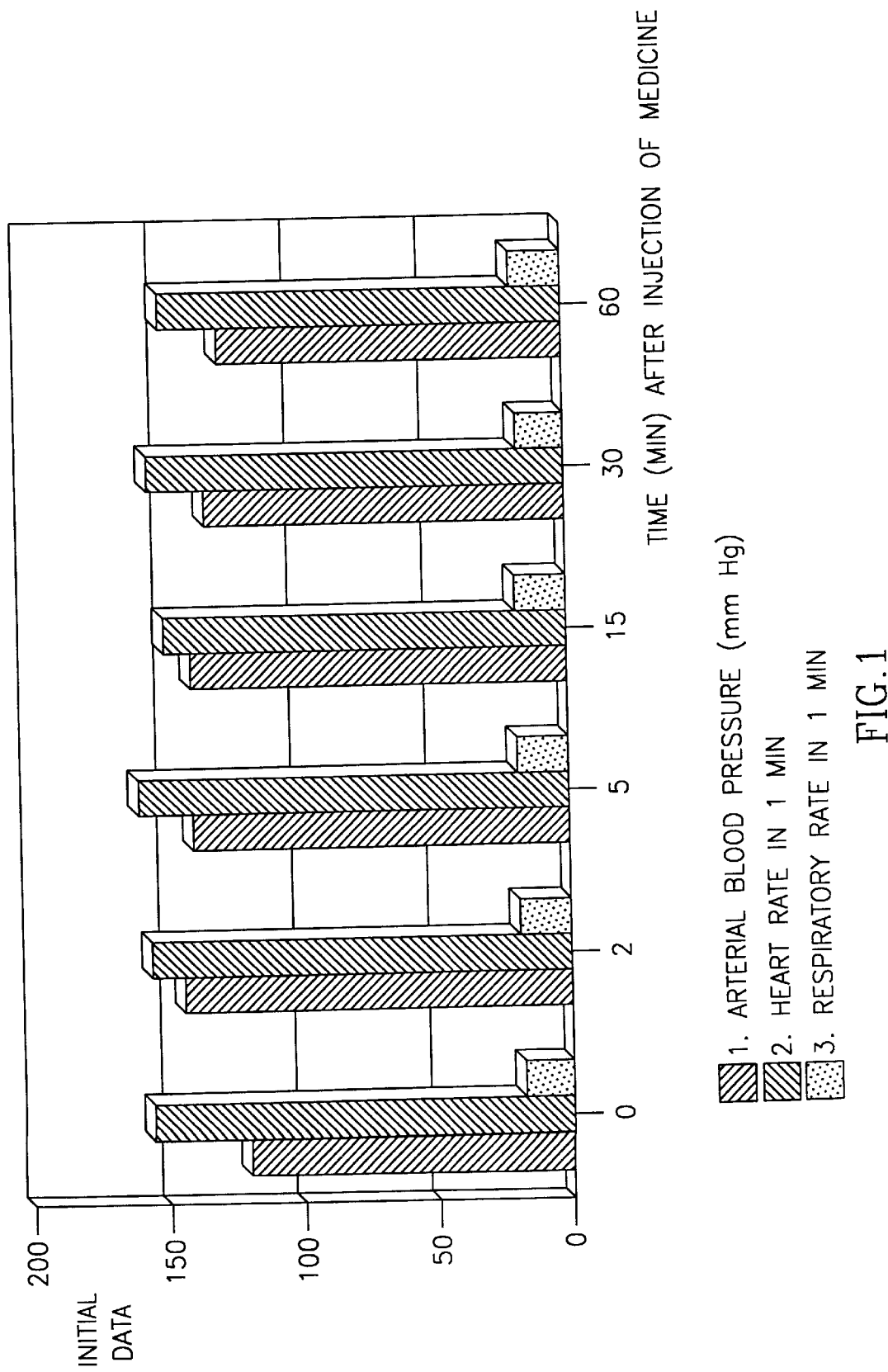
FIG. 1 shows the influence of a single intravenous injection of S-methylisothiouronium methylphosphite at a dose of 5 mg/kg, on arterial blood pressure, heart rate and respiratory rate.

S-methylisothiouronium methylphosphite increases arterial blood pressure by 20%. Hypertensive effect is retained for 1 hour. The compound does not influence HR (FIG. 1).

Figure 2:
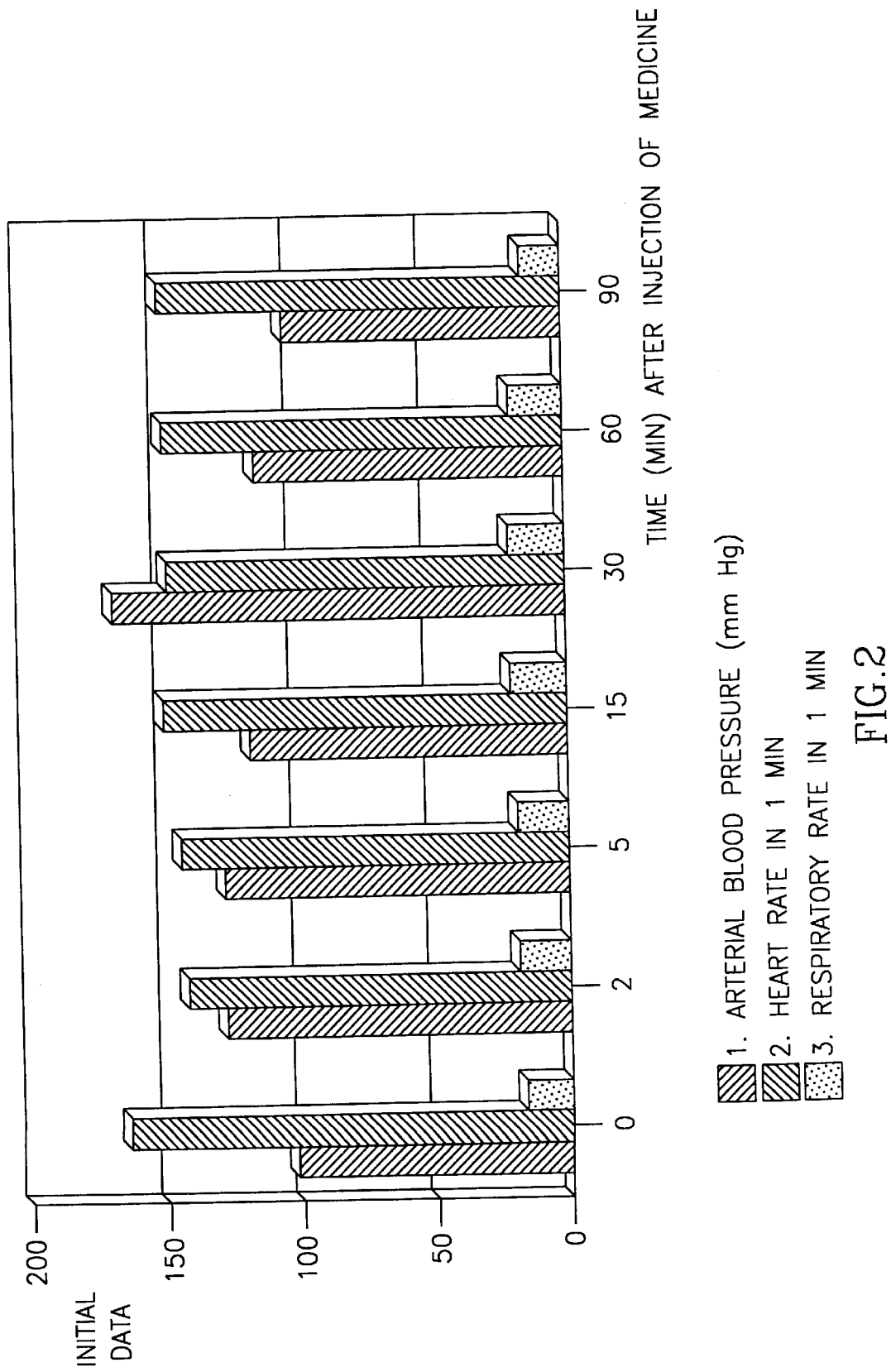
FIG. 2 shows the influence of a single intravenous injection of S-methylisothiouronium dimethylphosphate at a dose of 5 mg/kg, on arterial blood pressure, heart rate and respiratory rate.

S-methylisothiouronium dimethylphosphate is one of the most active compounds. It increases arterial blood pressure by almost 30%. Hypertensive effect is retained for 1.5 hour. The compound increases respiratory rate (RR) (FIG. 2).

Figure 3:
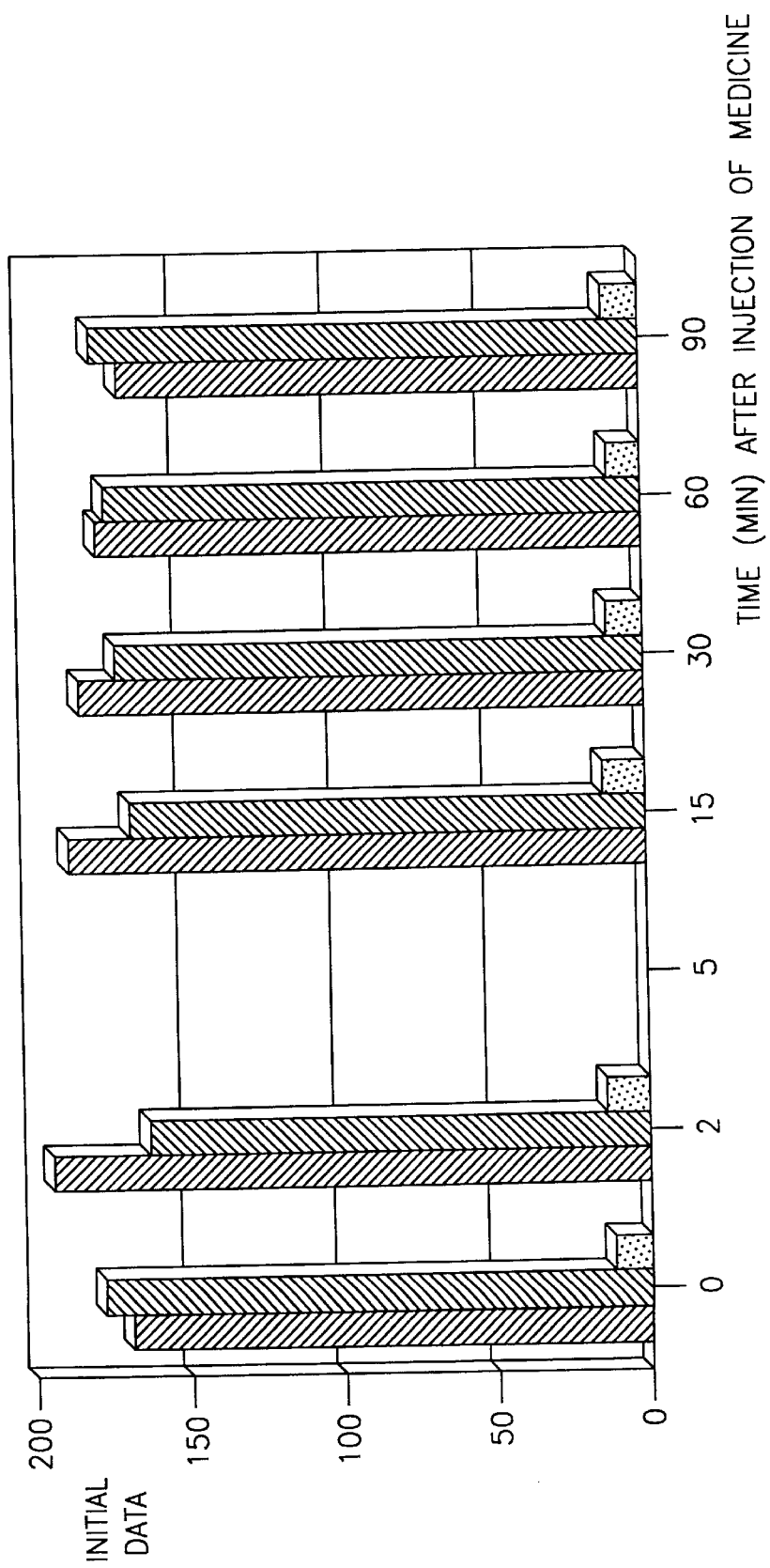
FIG. 3 shows the influence of a single intravenous injection of S-ethylisothiouronium metaphosphate at a dose of 5 mg/kg, on arterial blood pressure, heart rate and respiratory rate.

S-ethylisothiouronium metaphosphate increases arterial blood pressure by 25 mmHg, that is 15% of the initial level. Hypertensive effect is retained for 1.5 hours. The compound does not influence RR (FIG. 3).

Figure 4:
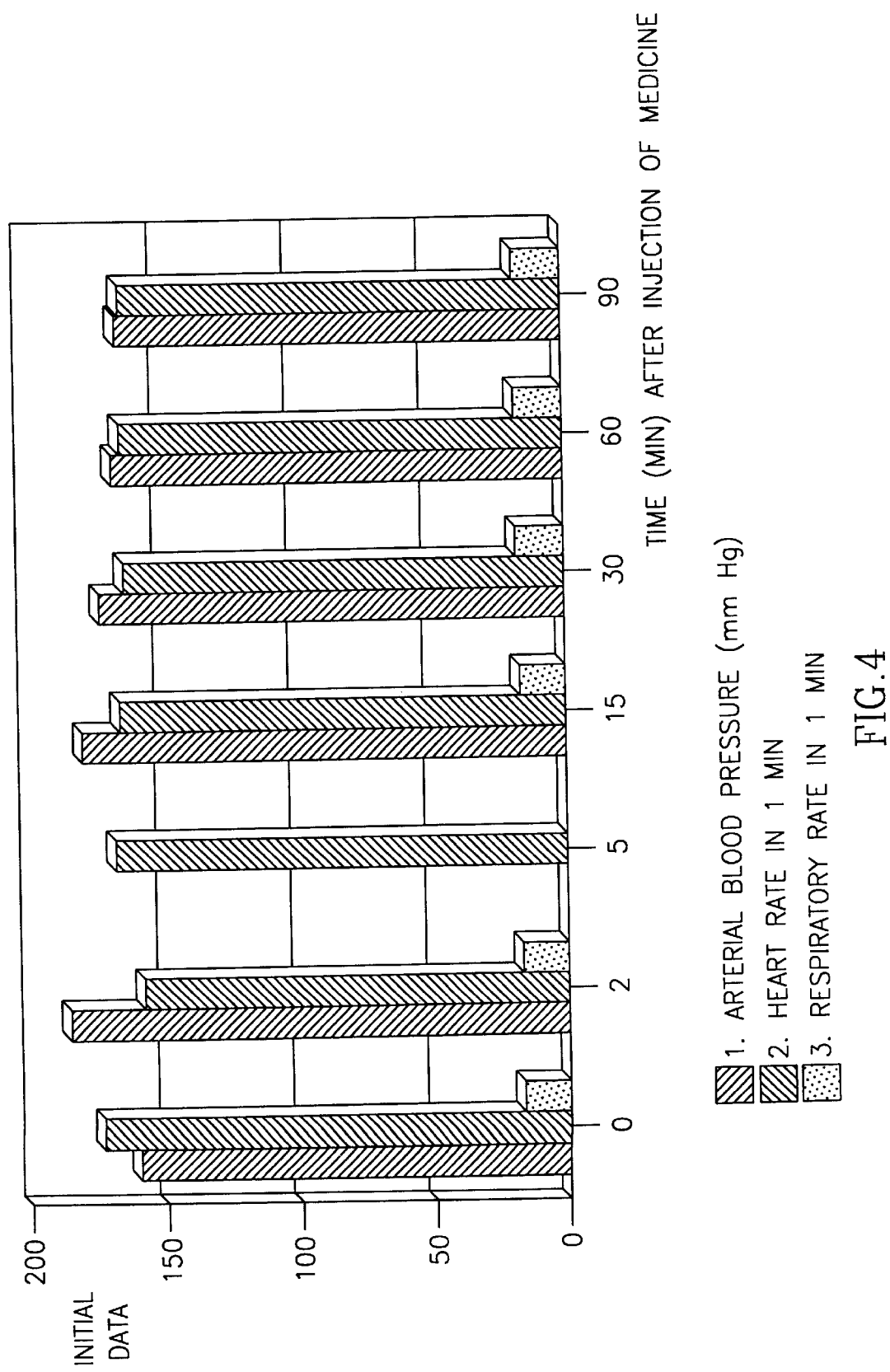
FIG. 4 shows the influence of a single intravenous injection of S-ethylisothiouronium ethylphosphite at a dose of 5 mg/kg, on arterial blood pressure, heart rate and respiratory rate.

S-ethylisothiouronium ethylphosphite increases arterial blood pressure by 15%. Duration of the effect is 1.5 hours. The compound causes bradycardia but does not influence RR (FIG. 4).

Figure 5:
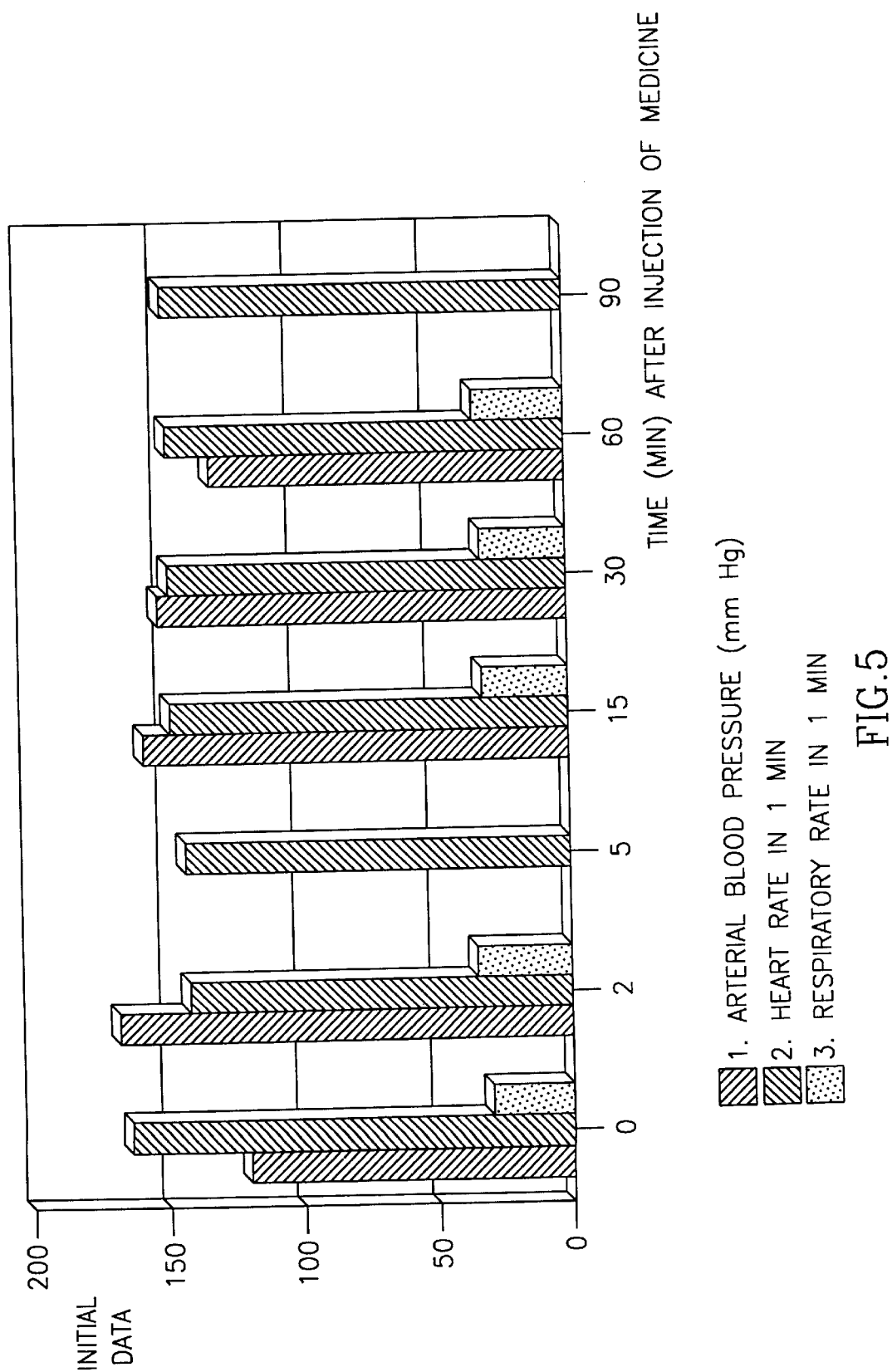
FIG. 5 shows the influence of a single intravenous injection of S-ethylisothiouronium diethylphosphate at a dose of 5 mg/kg, on arterial blood pressure, heart rate and respiratory rate.

S-ethylisothiouronium diethylphosphate (Difetur) is one of the most active compounds. The studied dose increases SAP by 40%. The compound increases RR (FIG. 5).

Figure 6:
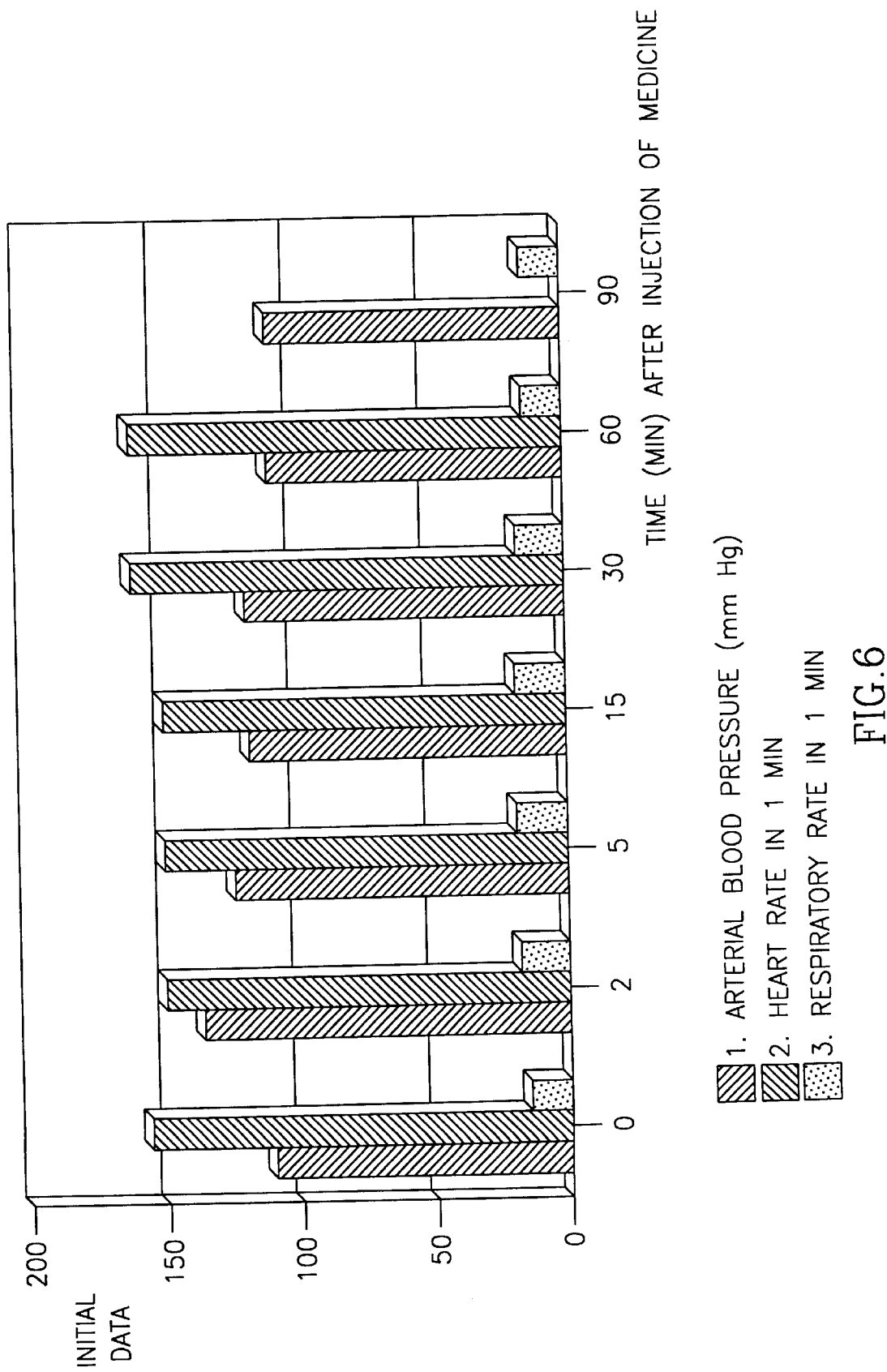
FIG. 6 shows the influence of a single intravenous injection of S-propylisothiouronium propylphosphite at a dose of 5 mg/kg, on arterial blood pressure, heart rate and respiratory rate.

S-propylisothiouronium propylphosphite increases arterial blood pressure by 24%. Hypertensive effect is retained for 1 hour. The compound causes moderate bradicardia but does not influence RR. (FIG. 6).

Figure 7:
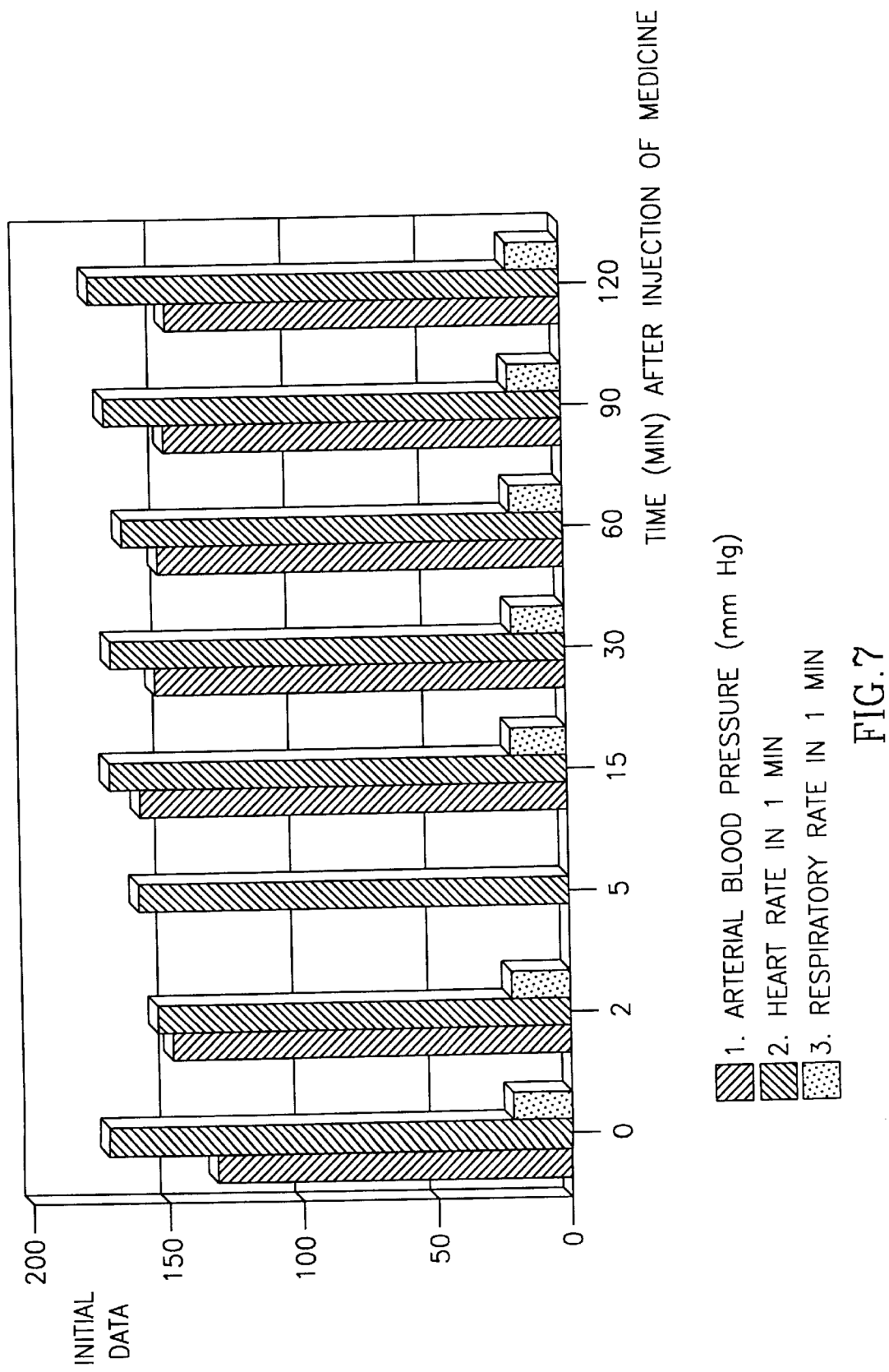
FIG. 7 shows the influence of a single intravenous injection of S-isopropylisothiouronium metaphosphate at a dose of 5 mg/kg, on arterial blood pressure, heart rate and respiratory rate.

S-isopropylisothiouronium metaphosphate slowly increases SAP. Maximum effect is observed only after 15 min., but the effect is retained during 2 hours and more. It does not influence RR (FIG. 7).

Figure 8:
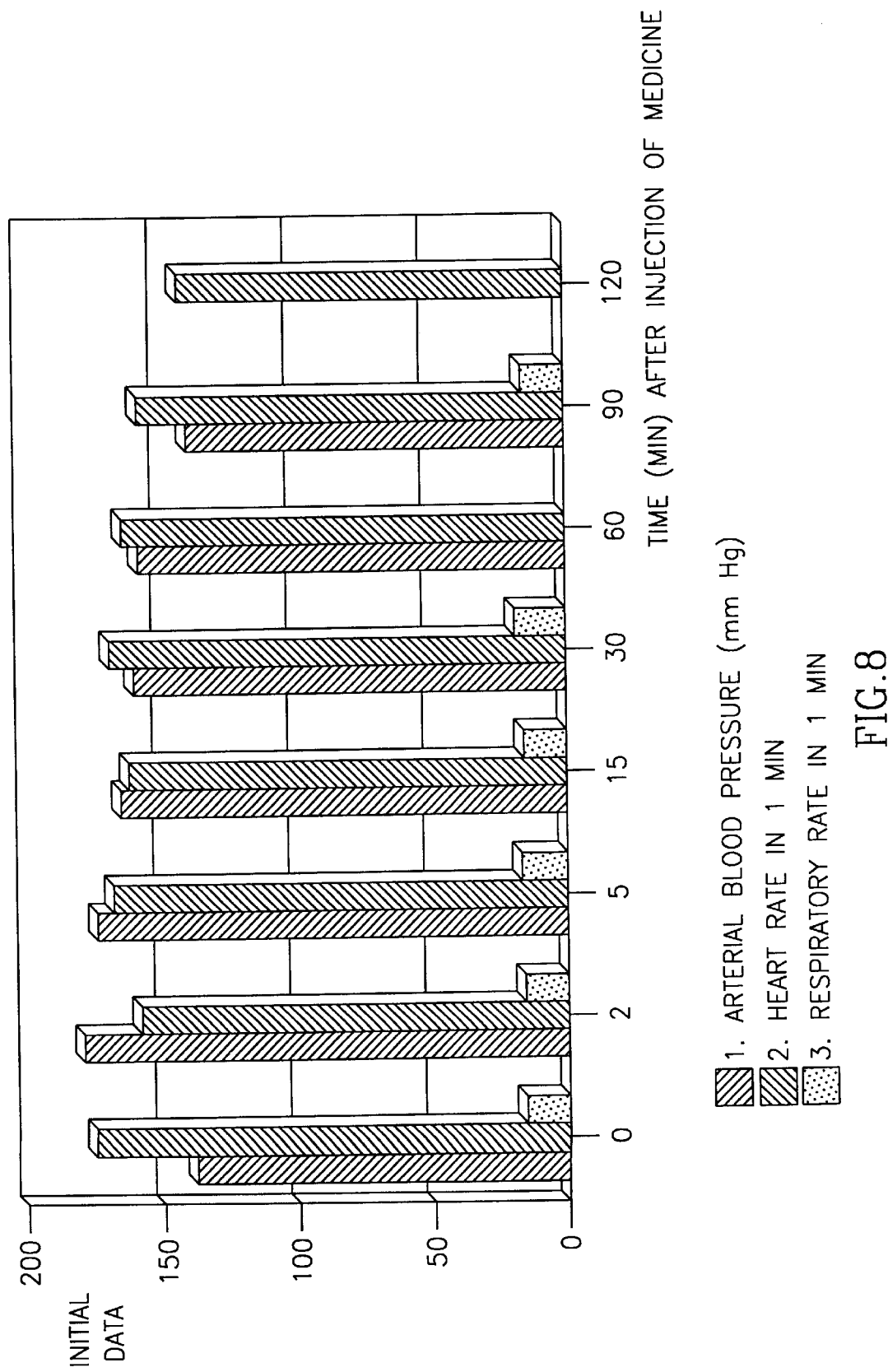
FIG. 8 shows the influence of a single intravenous injection of S-isopropylisothiouronium isopropylphosphite at a dose of 5 mg/kg, on arterial blood pressure, heart rate and respiratory rate.

S-isopropylisothiouronium isopropylphosphite is one of the most active substances. It increases SAP by almost 30%, maximum effect is already attained on the second minute after the injection and is retained for at least 2 hours. Transient bradycardia was noted. The compound does not influence RR (FIG. 8).

Figure 9:
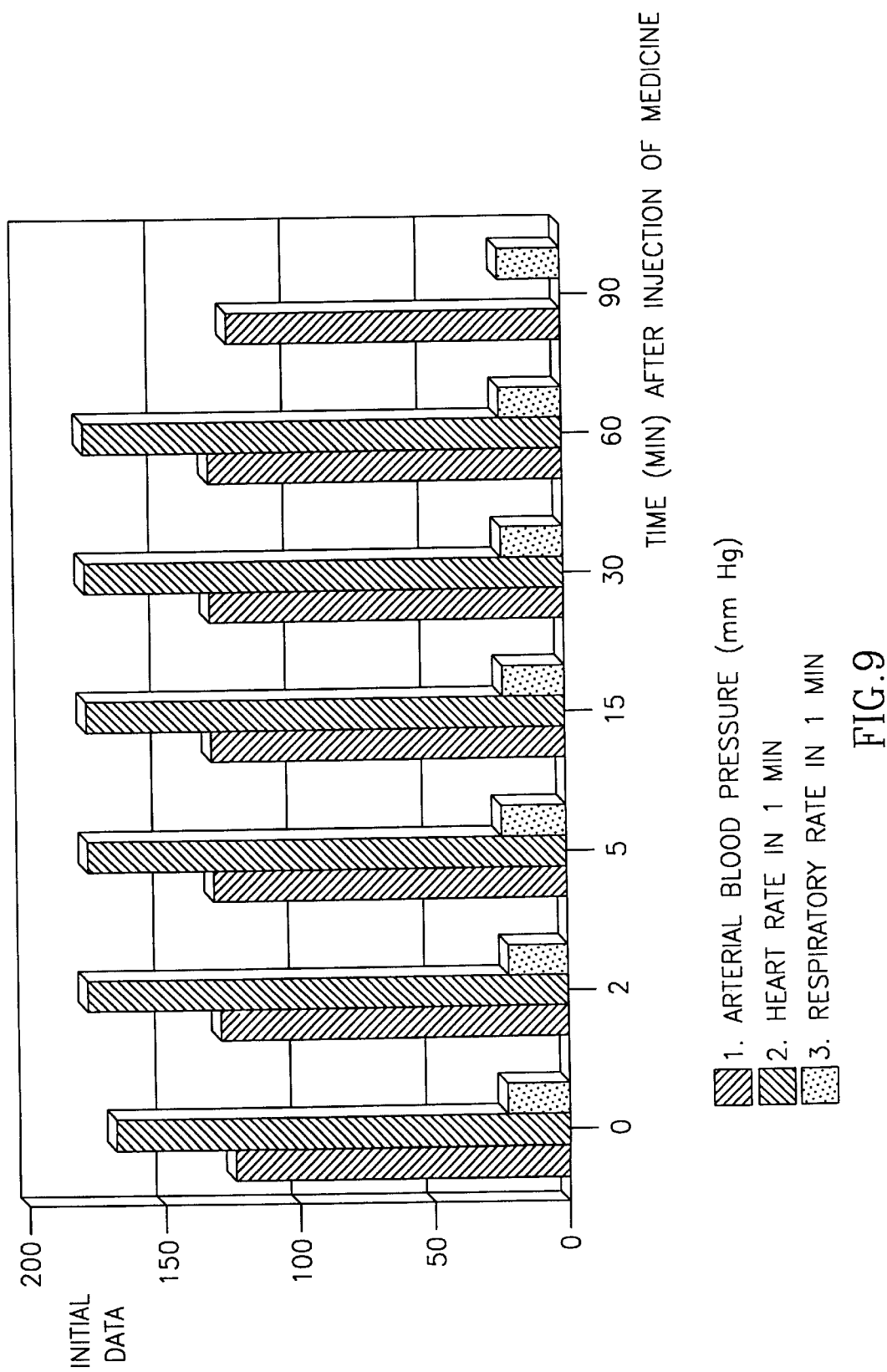
FIG. 9 shows the influence of a single intravenous injection of S-butylisothiouronium dibutylphosphate at a dose of 5 mg/kg, on arterial blood pressure, heart rate and respiratory rate.

S-butylisothiouronium dibutylphosphate slightly increases arterial blood pressure. Hypertensive effect is retained during 1 hour (FIG. 9).

Figure 10:
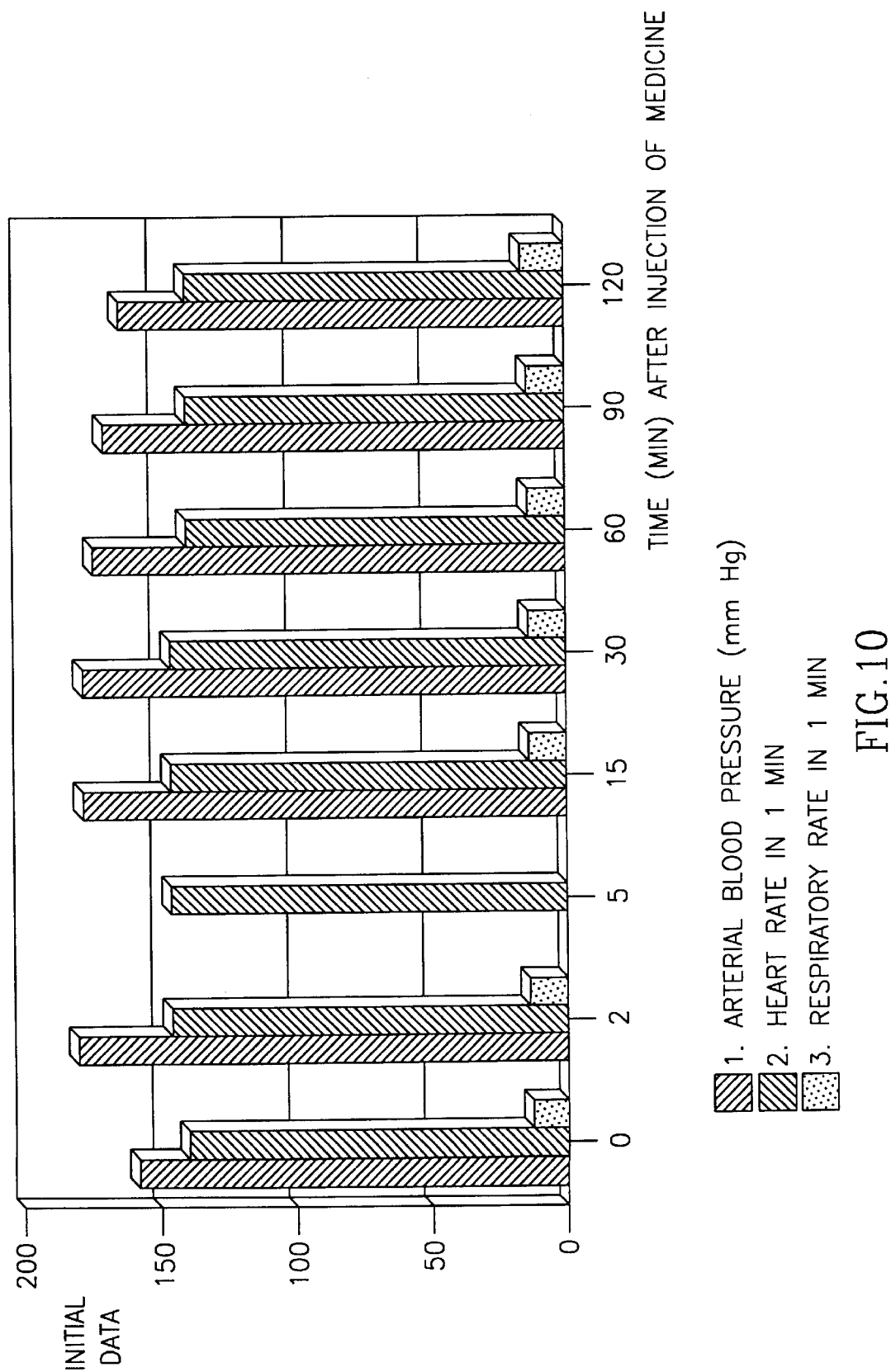
FIG. 10 shows the influence of a single intravenous injection of S-isobutylisothiouronium isobutylphosphite at a dose of 5 mg/kg, on arterial blood pressure, heart rate and respiratory rate.

S-isobutylisothiouronium isobutylphosphite exerts moderate hypertensive effect lasting for about 2 hours increasing HR and RR (FIG. 10).

The following results of experiments prove the high potential of S-ethylisothiouronium diethylphosphate as a drug affecting blood pressure.

An experimental study of the S-ethylisothiouronium diethylphosphate effect on the indices of system hemodynamics were performed on 8 narcotised cats with a body mass of 2–4 kg. Urethane (30% solution intraperitoneally, 1–1.2 g/kg) was used for narcostisation. To determine the period of maximum efficiency and duration of the preparation effect, the major parameters of the blood circulation were determined before its introduction (initial data) and on the 2nd, 15th, 30th, and 60th minute after the introduction, at a dose of 5 mg/kg.

The system hemodynamics was estimated on the basis of the following indices: arterial blood pressure (AP), heart rate (HR), minute volume of blood circulation (MVC), stroke volume of the heart (SV), total vascular peripheral resistance (PR), work of the left ventricle (Alv).

The arterial pressure was measured in the left cephalic artery of cats by a mercury pressure gauge. To prevent blood clotting, 0.2–0.3 ml (1000–1500 units) of heparin was injected intravenously. Heart rate was calculated according to the R—R interval of electrocardiogram. Recording was performed through two-channel electrocardiograph. MVC was calculated according to Ramirez A. A. et al. (1956). SV, ARV, and PR were calculated from the data on MVC, AP, central blood volume, and HR using C. G Wiggers formular (1947). Quantitative material obtained in the experiments was subjected to statistical analysis by the Student t-test. The results are listed in Table 2.

The experimental results, as summarized in Table 2, demonstrate that a single intravenous injection of S-ethylisothiouronium diethylphosphate at a dose of 5 mg/kg causes a quick increase of AP. Already on the second minute after the injection, AP increased by 41% relative to the initial level and remained at the elevated level for a long time. On the 60th minute AP level was lower in comparison to the level on the 30th minute but was still higher (by 11%) than the initial level. The differences in values characterizing AP level within an hour were statistically significant. Expression and duration of the AP increase depended mainly on the PR increase and to a lesser extent (on the 2nd minute of the medicine activity) on the MVC increase (Table 2).

On the 2nd minute after S-ethylisothiouronium diethylphosphate injection, PR reached 135% of the initial level and remained high throughout the experiment. On the 60th minute it was 58% higher than the initial value. Thus the overall tone of vascular resistance increased after the injection (Table 2). On the 2nd minute after medicine injection MVC increased by 7%, and on the 15th and 30th minutes decreased by 11% and 22% respectively. Such MVC changes were determined by the character of changes under the influence of the medicine—by the circulated blood volume, by the amount of the venous blood return to the heart and as a consequence, SV of the heart. Alv increase was transient on the 2nd and 15th minutes since it exceeded the initial value by 89% and 22%, and on the 30th minute it returned to the initial level. Test results show that hypertensive effect after a single S-ethylisothiouronium diethylphosphate intravenous injection and which lasts a prolonged time (up to 1 hour) depends mainly on PR and to a lesser extent (mainly in the initial period of the medicine activity) on the MVC increase.

It is known that adrenomimetics do not suppress hypotension caused by adrenergic blockers, except at high doses. It was of interest to study the influence of S-ethylisothiouronium diethylphosphate the in case of hypotension caused by the injection of a known α1-adreno blocker, namely prazosin. Prazosin was injected singly intravenously at a dose of 1 mg/kg. The results are listed in Table 3.

TABLE 2

Influence of a single intravenous injection of S-ethylisothiouronium diethylphosphate (5 mg/kg) on the system hemodynamic indices of cats (Average ± SD, n = 8)

| Hemodynamic Indices | Initial Data | Time after injection (min) | | | |
|---|---|---|---|---|---|
| | | 2 | 15 | 30 | 60 |
| AP, mm Hg | 119 ± 4.4 | 168 ± 9.9 | 158 ± 8.1 | 152 ± 8.4 | 132 ± 9.3 |
| P | | <0.01 | <0.01 | <0.01 | <0.05 |
| HF per min. | 176 ± 11.9 | 166 ± 17.9 | 178 ± 15.4 | 192 ± 11.9 | 188 ± 10.4 |
| P | | <0.05 | <0.05 | <0.05 | <0.05 |
| MVC, ml/min | 94.9 ± 4.9 | 101.9 ± 6.8 | 84.3 ± 5.7 | 74.1 ± 5.2 | 67.6 ± 8.4 |
| P | | <0.05 | <0.05 | <0.05 | <0.05 |
| $CO_2$, ml | 1.55 ± 0.24 | 2.14 ± 0.45 | 1.46 ± 0.25 | 1.23 ± 0.21 | 1.13 ± 0.26 |
| P | | <0.05 | <0.05 | <0.05 | <0.05 |
| PR, $10^3 \cdot din \cdot c \cdot cm^{-5}$/kg | 102.5 ± 6.1 | 138.6 ± 10.5 | 153.8 ± 7.1 | 168.5 ± 13.0 | 161.5 ± 14.1 |
| P | | <0.05 | <0.01 | <0.01 | <0.01 |
| Alv, g · cm | 257.6 ± 54.8 | 486.2 ± 136.8 | 317.1 ± 59.4 | 251.9 ± 50.3 | 211.3 ± 56.1 |
| P | | <0.05 | <0.05 | <0.05 | <0.05 |

Note:
P value relates to difference from initial data

TABLE 3

Influence of a single intravenous S-ethylisothiouronium diethylphosphate injection (5 mg/kg) on AP, HF, and respiratory rate on the background of acute arterial hypotension, caused by prazosin (1 mg/kg) (Average ± SD, n = 6)

| Indices | Initial Data | On the 5th min after prazosin injection | Time after injection | | | |
|---|---|---|---|---|---|---|
| | | | 2 | 15 | 30 | 60 |
| AP, mm Hg | 157.5 ± 3.2 | 106.3 ± 2.4 | 135.0 ± 5.6 | 118.8 ± 10.3 | 116.3 ± 4.8 | 110.0 ± 7.4 |
| $P_1$ | | <0.001 | | | | |
| $P_2$ | | | <0.05 | <0.05 | <0.05 | >0.05 |
| HF per min. | 171.6 ± 5.2 | 156.8 ± 9.0 | 152.4 ± 9.4 | 146.4 ± 5.6 | 144.0 ± 5.0 | 135.6 ± 7.0 |
| $P_1$ | | >0.05 | | | | |
| $P_2$ | | | >0.05 | >0.05 | >0.05 | <0.05 |
| Respiratory contraction frequency/min | 12.2 ± 1.5 | 13.6 ± 2.9 | 14.6 ± 3.9 | 12.4 ± 3.0 | 11.8 ± 2.3 | 11.0 ± 1.0 |
| $P_1$ | | >0.05 | | | | |
| $P_2$ | | | >0.05 | >0.05 | >0.05 | >0.05 |

Note:
$P_1$ - P value in relation to the initial data
$P_2$ - P value in relation to the data obtained on the 30th minute of the shock.

Due to the prazosin effect, vascular peripheral resistance substantially decreases and, consequently, also the AP level. Already on the 5th minute after prazosin injection, arterial pressure decreases by 51 mm Hg. On this background S-ethylisothiouronium diethylphosphate injection increases AP by 29 mm Hg already on the 2nd minute. On the 15th and 30th minutes AP level was 11.8% and 9.4% higher in comparison with the AP level on the 5th minute after adversuten injection. Statistically significant changes of HR and respiratory movement frequency were not observed (except for the 60th minute after S-ethylisothiouronium diethylphosphate injection when bradycardia was noted). Thus, it may be concluded that S-ethylisothiouronium diethylphosphate increases AP also on the background of α1-adreno blockers though with a lower duration than without them.

For the experimental model of hemorrhagic shock closely resembling acute clinical situations, acute blood loss in cats was chosen (3.2% of the body mass) which constitutes- 45–47% of the blood circulation volume during 3–5 minutes. To determine maximum efficiency and effective duration, parameters of the system blood circulation were determined before blood-letting and in 30 minutes after blood-letting, as well as on the 2nd, 10th, 30th and 60th minutes after intravenous injection of the medicine. The results are listed in Table 4.

TABLE 4

Influence of a single intravenous S-ethylisothiouronium diethylphosphate injection at a dose of 5 mg/kg on the system hemodynamic indices during hemorrhagic shock (Average ± SD, n = 6)

| Indices | Initial Data | On the 30$^{th}$ min of blood loss | Time after Injection (min) | | | |
| --- | --- | --- | --- | --- | --- | --- |
| | | | 2 | 10 | 30 | 60 |
| AP, mm Hg | 140.0 ± 3.9 | 65.0 ± 4.1 | 122.3 ± 6.0 | 112.5 ± 7.6 | 87.5 ± 15.4 | 84.2 ± 18.9 |
| $P_1$ | | <0.001 | | | | |
| $P_2$ | | | <0.01 | <0.01 | >0.05 | >0.05 |
| HF per min. | 165.0 ± 10.7 | 195.0 ± 16.5 | 182.0 ± 15.0 | 186.0 ± 14.1 | 179.1 ± 12.4 | 166.8 ± 15.2 |
| $P_1$ | | <0.05 | | | | |
| $P_2$ | | | <0.05 | >0.05 | >0.05 | >0.05 |
| MVC, ml/min . kg | 102.8 ± 4.5 | 44.0 ± 5.2 | 52.4 ± 6.0 | 46.0 ± 5.7 | 30.8 ± 5.5 | 35.7 ± 5.5 |
| $P_1$ | | <0.001 | | | | |
| $P_2$ | | | <0.05 | >0.05 | <0.05 | <0.05 |
| $CO_2$ ml | 2.2 ± 0.1 | 0.8 ± 0.1 | 1.0 ± 0.1 | 0.9 ± 0.1 | 0.6 ± 0.1 | 0.7 ± 0.1 |
| $P_1$ | | <0.001 | | | | |
| $P_2$ | | | <0.05 | >0.05 | <0.05 | >0.05 |
| Central blood volume, ml | 69.4 ± 7.4 | 51.6 ± 1.1 | 58.6 ± 4.1 | 49.2 ± 4.5 | 43.2 ± 4.7 | 45.5 ± 5.1 |
| $P_1$ | | >0.05 | | | | |
| $P_2$ | | | >0.05 | >0.05 | >0.05 | <0.05 |
| Pr, $10^3$ . din . c . cm$^{-3}$ | 107.7 ± 17.1 | 98.4 ± 14.7 | 202.8 ± 28.7 | 225.1 ± 56.6 | 244.7 ± 39.1 | 245.3 ± 62.6 |
| $P_1$ | | >0.5 | | | | |
| $P_2$ | | | <0.01 | <0.01 | <0.01 | <0.01 |
| Number of blood circulations, min | 5.2 ± 0.2 | 2.9 ± 0.2 | 2.9 ± 0.2 | 3.0 ± 0.2 | 2.4 ± 0.3 | 3.5 ± 0.2 |
| $P_1$ | | <0.01 | | | | |
| $P_2$ | | | >0.05 | >0.05 | >0.05 | >0.05 |
| ALV, g/cm | 413.9 ± 0.2 | 69.5 ± 8.4 | 166.6 ± 18.4 | 130.5 ± 15.4 | 75.9 ± 19.4 | 77.0 ± 17.0 |
| $P_1$ | | <0.01 | | | | |
| $P_2$ | | | <0.001 | <0.01 | >0.05 | >0.05 |

Note:
$P_1$ - P value in relation to the initial data
$P_2$ - P value in relation to the data obtained on the 30$^{th}$ minute of the blood loss.

In the control group (8 cats), the blood loss caused an AP drop from 140.0±3.9 to 65.0±4 mm Hg which constitutes 46% of the initial level. HR increased by 18% on the 30th minute after beginning of blood loss. MVC decreased from 102.8±4.5. to 44.0±5.2 ml/min., i.e. by 57% in comparison with the initial value.

AP decrease on the 30th minute after beginning of acute blood loss was caused mainly by the MVC decrease which in its turn depended on the decrease of the stroke volume (to 36%) and central blood volume. Thus posthemorrhagic hypovolemia leads to the MVC decrease, which cannot be compensated by the PR and heart rate increase.

On the 2nd minute after the introduction of isotonic solution the system hemodynamic indices slightly differed from those on the 30th minute after the acute blood loss began. However on the 10 and 30th minute after the injection of 1 ml of sodium chloride isotonic solution, system hemodynamic indices progressively deteriorated. Thus on the 30th minute after the solution injection AP decreased by 13% in comparison with the 30 minute after bleeding began. HR decreased by 7%, while MVC and SV decreased by 11% and 8% respectively. Alv decreased by the half, while PR increased by 8%. Further MVC decrease caused by the reduction of the left ventricular productivity led to the animals death.

Single intravenous introduction of S-ethylisothiouronium diethylphosphate at a dose of 5 mg/kg in the case of hemorrhagic shock causes a quick increase in AP. Thus on the 2nd minute after the medicine injection AP increased by 88% (compared to the 30th minute after bleeding in the control group), and this effect was retained during the whole period of observation. On the 2nd minute after the S-ethylisothiouronium diethylphosphate injection, the decrease in HR was noted. The latter can be explained as a reflux influence on the heart as a result of a sharp AP increase. S-ethylisothiouronium diethylphosphate has a 2-phase influence on MVC. Initially MVC increases by 19% with subsequent decrease on the 30th and 60th minutes after the medicine injection. However it should be noted that in a control group, after the injection of 1 ml of isotonic solution the same MVC decrease was observed on the 30th and 60th minutes. SV increased only on the 2nd minute after the medicine injection. Alv essentially increased on the 2nd and 10th minutes. PR increased during the whole period of observation.

When analyzing the changes in the system hemodynamic indices under the influence of S-ethylisothiouronium diethylphosphate, it may be concluded that the substance increases AP in the initial period due to MVC and PR increase and in the later period due to PR increase.

The influence of S-ethylisothiouronium diethylphosphate on the background of arterial hypotension caused by a known ganglion blocker-hexamethonium has been studied in cats. Hexamethonium was injected intra- venously at a dose of 10 mg/kg. Vagus and schiatic nerve stimulation was carried out by electrical pulsator with the above-threshold rectangular pulse current having a duration of 1 msec, irritation time of 10 sec, and frequency of 20 pulses/sec (peripheral section of the vagus nerve), and frequency of 300 pulses/sec (central end of the schiatic nerve). The results are listed in Table 5.

had a two-fold character. Five of seven cats had metabolic and respiratory acidosis, two had metabolic acidosis with compensated respiratory alkalosis. pH of arterial blood decreased on the average from $7.313\pm0.015$ in the initial state to $7.284\pm0.033$ on the 30th minute after blood loss

TABLE 5

Influence of a single intravenous injection of S-ethylisothiouronium diethylphosphate at a dose of 5 mg/kg on AP, HF on the background of acute arterial hypotension, caused by the hexamethonium administration (Average ± SD, n = 6)

| Indices | Initial Data | On the 2$^{nd}$ min after hexonium injection | Time after injection | | | |
|---|---|---|---|---|---|---|
| | | | 2 | 15 | 30 | 60 |
| AP, mm Hg | 159.0 ± 5.6 | 91.0 ± 10.0 | 152.0 ± 4.6 | 147.0 ± 7.8 | 146.8 ± 4.8 | 143.0 ± 7.2 |
| P$_1$ | | <0.01 | | | | |
| P$_2$ | | | <0.01 | <0.05 | <0.05 | <0.05 |
| HF per min. | 139.2 ± 5.0 | 137.6 ± 13.4 | 120.0 ± 12.0 | 105.6 ± 11.6 | 109.2 ± 11.1 | 108.0 ± 15.8 |
| P$_1$ | | <0.05 | | | | |
| P$_2$ | | | >0.05 | >0.05 | >0.05 | >0.05 |

Note:
P$_1$ - P value in relation to the initial data
P$_2$ - P value in relation to the data obtained on the 2$^{nd}$ minute after injection of hexamethanium 2 minutes after hexamethonium injection, AP decreased by 46%. Injection of S-ethylisothiouronium diethylphosphate increased AP by 61 mm Hg already on the 2nd minute, and the increase AP persisted during the period of observation. HR changed to the direction of bradycardia, however, those changes were not statistically significant. Respiratory rate did not change. When S-ethylisothiouronium diethylphosphate was injected, ganglion blocking properties are completely retained which is testified by the absence of changes in the AP levels when the peripheral section of the vagus and central end of schiatic nerve were repeatedly (on the 2nd, 15th, 30th, and 60th minute) irritated.

It may be concluded that S-ethylisothiouronium diethylphosphate quickly restores the AP level after the ganglion blocker caused hypotension and maintains it for a long time.

The influence of S-ethylisothiouronium diethylphosphate on the major indices of the blood acid-base state (AAS) and gas content in hemorrhagic shock was studied at a dose of 5 mg/kg. The cats were narcotized intraperitoneally with pentobarbital sodium (nembutal) at a dose of 40 mg/kg. The blood loss was caused by blood-letting from the common carotid artery in an amount of 3.2% of the animal body mass, which approximately corresponds to 45–47% of the blood circulation volume. The blood-letting was carried out during 3–5 minutes. Tension characteristics of oxygen and carbon dioxide in arterial (PaO$_2$, PaCO$_2$) and mixed venous (PvO$_2$, PvCO$_2$) blood, pHa and pH were studied by Astrup micromethod. The hemoglobin content (Hb) was determined by the cianohemoglobin method. Bicarbonate ion content /HCO$_3$ was calculated with the help of the Severinghause ruler. Calculations were carried out on the CM-1403-02 computer in the Forhtran language program. Indices of the acid-base balance and blood gas content were studied in the initial state, on the 30th minute after acute bleeding as well as on 2nd, 10th, 30th, and 60th minute after the medicine injection. The substance was injected singly intravenously on the 30th minute after the blood-letting.

In the control group (n=8), cats were injected with 1 ml of isontonic solution of sodium chloride.

Experimental results revealed that the changes in the acid-base balance of arterial blood in the control group cats with acute blood loss on the 30th minute after blood-letting beginning. On the 40th and 60th minute after blood-letting, pHa further decreased to $7.242\pm0.056$ and $7.152\pm0.072$ respectively was registered. A more expressed pH decrease was registered in venous blood. Thus, in seven out of eight cats, the pH decreased to the 30th minute after blood loss and in one cat it did not essentially change. pHv decreased from $7.284\pm0.011$ in the initial state to $7.184\pm0.028$, $7.127\pm0.049$, and $7,081\pm0.049$ respectively on the 30th, 40th, and 60th minute after blood-letting (p<0.05).

After acute blood loss, the metabolic indices of acid-base balance of arterial and venous blood decreased during the whole period of observation. Bicarbonate ion content in arterial blood reduced on the 30th, 40th and 60th minute after blood loss by 25%, 27%, and 40% respectively in comparison with the initial data (p<0.001). Parallel to this, a decrease in BE was found from $6.97\pm0.70$ mmol/l in the initial state to $10.61\pm0.86$ mmol/l on the 30th minute after the blood loss (P<0.01). Further to the 30th and 60th minute from the beginning of bleeding, this index decreased by 87.7% and 143% respectively. The same changes in [HCO$_3$] and [BE] content were found in venous blood. Thus on the 30th minute after the blood loss, the carbonate ion content [pHCO$^-_3$] was 14.6% lower than of the control. The basis deficiency increased on the 30th, 40th and 60th minute after acute blood loss by 55%, 99%, and 130% respectively in comparison with the initial index (P<0.01). Thus, according to our results, the most frequent form of the acid-base balance disturbance on the earlier stages after massive acute blood loss is metabolic acidosis.

On the 30th minute after acute blood loss, decrease in PaCO$_2$ and a slight increase in PvCO$_2$ were noted which led to the increase of arterial-venous gradient PCO$_2$ in comparison with the initial level. It is obvious that the gradient decrease observed in the acute blood loss dynamics significantly worsened conditions of gas exchange in lungs and in tissues and led to the acute increase of metabolic and respiratory acidosis. The degree of the arterial blood oxygenation in the control group is quite high, while venous blood PO$_2$ decreased.

In the test group (n=6), S-ethylisothiouronium diethylphosphate was injected at a dose of 5 mg/kg.

Table 6 demonstrates that in cats with hemorrhagic shock, S-ethylisothiouronium diethylphosphate corrects the metabolic acidosis caused by the loss of blood; after the S-ethylisothiouronium diethylphosphate injection, pH of arterial blood increases from 7.230±0.015 on the 30th minute of blood letting to 7.252±0.018 and 7.310±0.064 on the 10th and the 30th minute respectively.

TABLE 6

Influence of a single intravenous S-ethylisothiouronium diethylphosphate injection at a dose of 5 mg/kg on the major indices of the acid-base balance and gas composition of arterial blood in condition of hemorrhagic shock (Average ± SD, n = 6)

| Indices | Initial Data | On the 30$^{th}$ min of shock | Time after injection (min) | | |
|---|---|---|---|---|---|
| | | | 10 | 30 | 60 |
| pHa | 7.290 ± 0.02 | 7.230 ± 0.015 | 7.252 ± 0.018 | 7.310 ± 0.064 | 7.208 ± 0.036 |
| $P_1$ | | <0.05 | | | |
| $P_2$ | | | <0.05 | <0.05 | <0.05 |
| Carbonic acid gas tension (PaCO$_2$), mm Hg | 38.516 ± 2.051 | 31.633 ± 2.366 | 28.616 ± 2.858 | 31.083 ± 1.933 | 35.217 ± 7.339 |
| $P_1$ | | <0.05 | | | |
| $P_2$ | | | <0.05 | >0.05 | >0.05 |
| Buffer bases (Bba), mmol/l | 36.400 ± 2.660 | 32.500 ± 1.396 | 34.150 ± 1.364 | 34.966 ± 3.534 | 32.733 ± 5.616 |
| $P_1$ | | >0.05 | | | |
| $P_2$ | | | >0.05 | >0.05 | >0.05 |
| Buffer bases shift (Bea), mmol/l | −5.283 ± 0.424 | −9.866 ± 0.949 | −7.866 ± 1.095 | −8.016 ± 1.436 | −9.450 ± 3.903 |
| $P_1$ | | <0.01 | | | |
| $P_2$ | | | <0.05 | <0.05 | >0.05 |
| Bicarbonate ion content (HCO$_3$a), mmol/l | 19.300 ± 0.949 | 14.766 ± 0.995 | 15.583 ± 1.333 | 17.083 ± 1.065 | 15.900 ± 3.033 |
| $P_1$ | | <0.01 | | | |
| $P_2$ | | | >0.05 | <0.05 | >0.05 |
| Oxygen tension (PaO$_2$) | 85.183 ± 5.281 | 88.533 ± 8.433 | 94.483 ± 6.012 | 95.466 ± 7.144 | 85.550 ± 6.575 |
| $P_1$ | | >0.5 | | | |
| $P_2$ | | | >0.05 | >0.05 | >0.05 |

Note:
$P_1$ - P value in relation to the initial data
$P_2$ - P value in relation to the data obtained on the 30$^{th}$ minute of the shock.

The bicarbonate ion content of arterial blood increased on the 10th and 30th minute after S-ethylisothiouronium diethylphosphate injection by 5% and 16% respectively compared to the initial values (Table 6).

Similar changes were observed in the major indices of the acid-base balance of mixed venous blood, however those changes were not statistically significant.

It may be also assumed that S-ethylisothiouronium diethylphosphate affects the indices of the blood acid-base balance by liberating the organism from metabolic final products, specifically from lactic acid, due to its more active involvement in the Cori and Crebs cycles, supporting conjugation of oxidation and phosphorylation.

The partial pressure of carbon dioxide in arterial and venous blood decreased after injection of S-ethylisothiouronium diethylphosphate on the 10th and 30th minute compared to the 30th minute after blood letting. Thus, on the 10minute it decreased by 9% (Table 6, Table 7). Partial pressure of oxygen in arterial and venous blood changed diversely under the influence of S-ethylisothiouronium diethylphosphate: it had the tendency to increase in the arterial blood, and to decrease in the venous blood. However, those variations were not statistically significant.

TABLE 7

Influence of a single intravenious S-ethylisothiouronium diethylphosphate injection at a dose of 5 mg/kg on the major indices of the acid-base balance and gas composition of mixed venous blood in condition of hemorrhagic shock (Average ± SD, n = 6)

| Indices | Initial Data | On the 30$^{th}$ min of shock | Time after injection (min) | | |
|---|---|---|---|---|---|
| | | | 10 | 30 | 60 |
| pHv | 7.257 ± 0.023 | 7.238 ± 0.026 | 7.252 ± 0.011 | 7.222 ± 0.016 | 7.150 ± 0.130 |
| $P_1$ | | >0.05 | | | |
| $P_2$ | | | >0.05 | >0.05 | <0.05 |
| Carbonic acid gas tension (PaCO$_2$), mm Hg | 45.600 ± 2.265 | 44.533 ± 4.008 | 40.516 ± 4.340 | 40.350 ± 4.611 | 55.533 ± 5.049 |
| $P_1$ | | >0.05 | | | |
| $P_2$ | | | <0.05 | <0.05 | <0.05 |
| Buffer bases (BBa), mmol/l | 37.700 ± 1.273 | 36.166 ± 2.583 | 34.500 ± 2.342 | 32.266 ± 3.254 | 33.833 ± 3.943 |
| $P_1$ | | >0.05 | | | |
| $P_2$ | | | >0.05 | >0.05 | >0.05 |
| Buffer bases shift (BBa), mmol/l | −6.516 ± 0.666 | −9.700 ± 1.396 | −8.500 ± 1.491 | −9.966 ± 1.388 | −11.266 ± 2.569 |
| $P_1$ | | <0.05 | | | |
| $P_2$ | | | >0.05 | >0.05 | >0.05 |

TABLE 7-continued

Influence of a single intravenious S-ethylisothiouronium diethylphosphate injection at a dose of 5 mg/kg on the major indices of the acid-base balance and gas composition of mixed venous blood in condition of hemorrhagic shock (Average ± SD, n = 6)

| Indices | Initial Data | On the 30$^{th}$ min of shock | Time after injection (min) | | |
|---|---|---|---|---|---|
| | | | 10 | 30 | 60 |
| Bicarbonate ion content (HCO$_3$a), mmol/l | 19.533 ± 0.691 | 16.850 ± 1.761 | 17.116 ± 1.576 | 16.150 ± 1.951 | 17.800 ± 2.162 |
| P$_1$ | | >0.05 | | | |
| P$_2$ | | | >0.05 | >0.05 | >0.05 |
| Oxygen tension (PvO$_2$) | 56.700 ± 6.988 | 46.366 ± 12.056 | 41.866 ± 11.242 | 40.533 ± 11.332 | 27.783 ± 4.824 |
| P$_1$ | | >0.5 | | | |
| P$_2$ | | | >0.05 | <0.05 | <0.05 |

Note:
P$_1$ - P value in relation to the initial data
P$_2$ - P value in relation to the data obtained on the 30$^{th}$ minute of the shock.

In the following tests, the effect of S-ethylisothiouronium diethylphosphate was studied on the cardiovascular system of dogs. AP was measured by two methods: it was registered on the tail artery by means of a piezosensor (Ugo Bazile pressure gauge) and in the thigh artery by a catheter filled with heparin. Electrocardiogram was registered in three standard branches.

Figure 11:
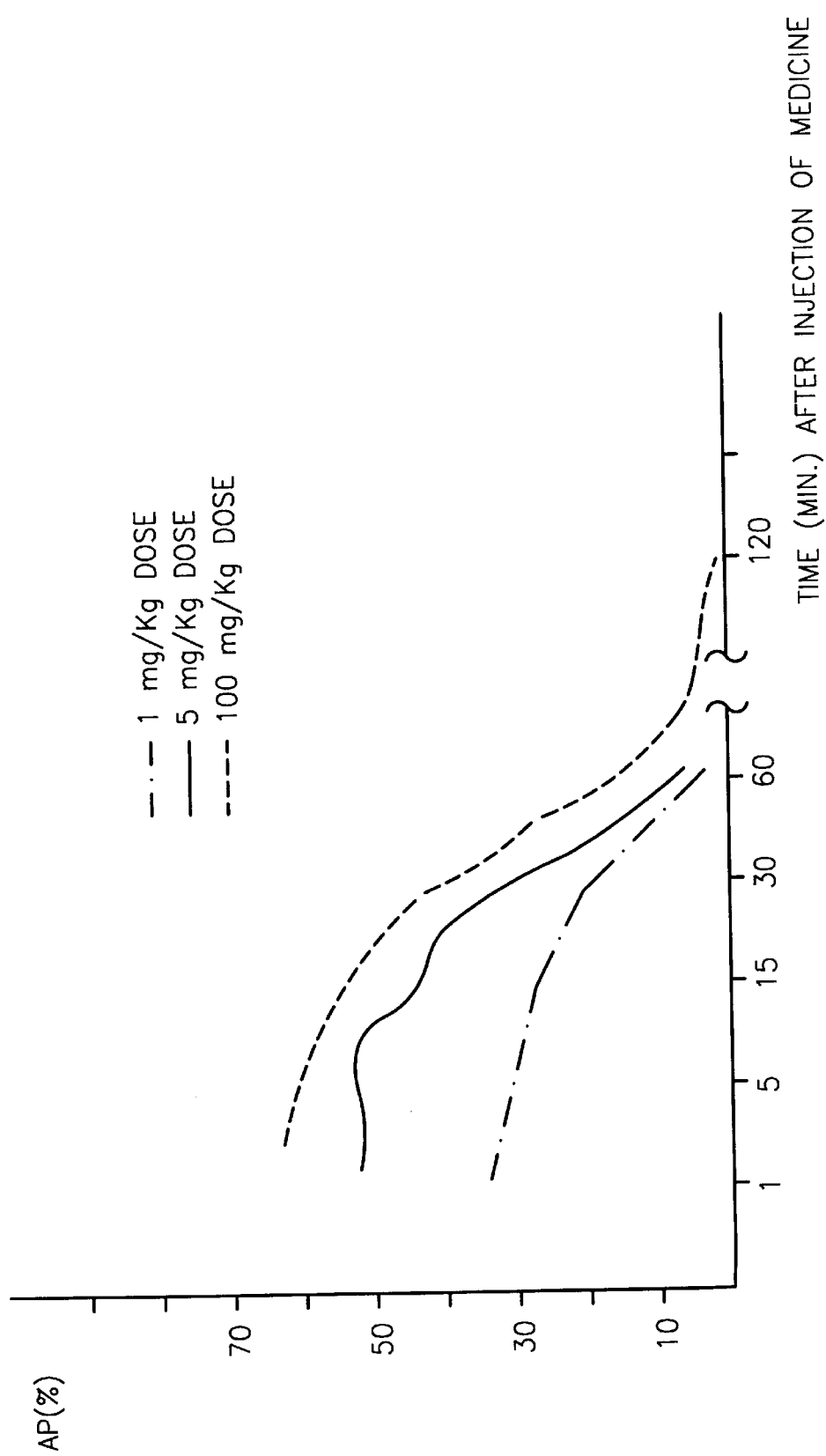
FIG. 11 shows the changes in arterial blood pressure (percent increase relative to the initial value) in dogs after a single intravenous S-ethylisothiouronium diethylphosphate injection at various doses.

FIG. 11 shows the optimization of the dosage of the preparation, when injected intravenously. S-ethylisothiouronium diethylphosphate was injected at doses of 1 mg/kg (n=5), 5 mg/kg (n=18), and 100 mg/kg (n=8). As shown in FIG. 11, S-ethylisothiouronium diethylphosphate has a pronounced hypertensive effect at all the doses used, 5–10 mg/kg probably being the optimal dose. The electrocardiogram did not reveal any pathological changes with all above mentioned doses. The development of a bradycardiac effect was noted which started already on the first minutes after the injection, reaching on the average 25–30% of the initial level. Maximal bradycardiac value was observed on the 30th–40th minutes after the experiment started and maintained till the 60th minute of the observation.

It was noted that the degree of the hypertensive reaction expression in dogs with low arterial pressure level (hypotensives) is significantly higher than in dogs with initially high arterial pressure level (hypertensives). Due to this fact the study was carried out separately for normotonics and hypotonics.

FIGS. 12 and 13 show AP indices when various doses of S-ethylisothiouronium diethylphosphate are injected. The data in these figures confirm that the hypertensive reaction in dogs with low arterial pressure is stronger and more prolonged. The optimal dose of S-ethylisothiouronium diethylphosphate when introduced intravenously is 5–10 mg/kg.

The effect of S-ethylisothiouronium diethylphosphate on body constituents was estimated in chronic and acute experiments. These experiments were conducted on F1 (C57B1× CBA) line mice and biochemical tests were made after a single administration of S-ethylisothiouronium diethylphosphate, injected intravenously at doses of 100 mg/kg (in the chronic experiment) and 500 mg/kg (in the acute experiment). The results are summarized in Tables 8 and 9.

TABLE 8

Influence of a single intravenous injection of S-ethylisothiouronium diethylphosphate at a dose of 500 mg/kg on the biochemical indices of mice blood serum (Average ± SD, n = 5)

| Indices | Initial Data | Time after injection (min) | | |
|---|---|---|---|---|
| | | 30 | 60 | 75 |
| Total protein | 78.3 ± 1.9 | 99.0 ± 4.3 | 89.4 ± 4.6 | 87.6 ± 3.8 |
| P | | | | |
| Total cholestrol, mmol/l | 3.6 ± 0.6 | 7.8 ± 1.2 | 7.2 ± 1.6 | 5.4 ± 1.2 |
| P | | | | |
| Glucose mmol/l | 7.6 ± 1.1 | 13.4 ± 2.6 | 9.0 ± 0.8 | 6.6 ± 1.0 |
| P | | | | |
| Body mass, g | 25.0 ± 3.8 | 24.8 ± 1.2 | 26.1 ± 1.8 | 26.0 ± 0.5 |
| P | | | | |

Note:
P value relates to a difference from initial data

TABLE 9

Influence of a single intravenous injection of S-ethylisothiouronium diethylphosphate at a dose of 100 mg/kg on the biochemical indices of mice blood serum (Average ± SD, n = 5)

| Indices | 1$^{st}$ day | | 7$^{th}$ day | | 14$^{th}$ day | | 21$^{st}$ day | |
|---|---|---|---|---|---|---|---|---|
| | Control | Experimental | Control | Experimental | Control | Experimental | Control | Experimental |
| Total protein | 64.2 ± 2.2 | 75.6 ± 4.9 | 72.6 ± 5.6 | 63.5 ± 4.4 | 70.9 ± 3.8 | 72.4 ± 3.3 | 80.3 ± 10.9 | 74.9 ± 2.4 |
| P | | | | | | | | |
| Total cholestrol, mmol/l | 3.6 ± 0.8 | 4.7 ± 0.9 | 4.8 ± 0.54 | 5.0 ± 0.6 | 4.2 ± 1.2 | 3.0 ± 0.36 | 3.3 ± 0.6 | 4.9 ± 0.42 |
| P | | | | | | | | |

TABLE 9-continued

Influence of a single intravenous injection of S-ethylisothiouronium diethylphosphate at a dose of 100 mg/kg on the biochemical indices of mice blood serum (Average ± SD, n = 5)

|  | 1st day | | 7th day | | 14th day | | 21st day | |
|---|---|---|---|---|---|---|---|---|
| Indices | Control | Experimental | Control | Experimental | Control | Experimental | Control | Experimental |
| Glucose mmol/l P | 7.5 ± 2.4 | 7.1 ± 1.4 | 8.2 ± 2.4 | 8.2 ± 1.8 | 7.2 ± 1.6 | 8.8 ± 1.7 | 8.7 ± 1.3 | 9.9 ± 1.8 |
| Body mass, g P | 26.0 ± 0.8 | 23.8 ± 0.1 | 26.0 ± 0.1 | 24.0 ± 0.2 | 28.0 ± 0.4 | 28.1 ± 0.3 | 26.5 ± 0.5 | 26.1 ± 0.5 |

Note: $P_1$ - P value relates to a difference from initial data

In the acute experiment, blood was taken 30, 60 and 75 minutes after the administration of the medicine. In the chronic experiment (which lasted 30 days), blood was daily examined 1 hour after the injection. Terms of the study were 1, 7, 14, and 21 days. The concentrations of total protein, total cholesterol, and glucose in mice blood serum were determined by conventional methods. Total protein was determined by a biuret method, total cholesterol—by like method, glucose—by the glucose-oxidase method.

Mouse blood was obtained after rapid decapitation. Tested material was sampled at the same time of the day and on the same season.

Blood for serum was sampled into centrifuge test tubes, put into the thermostat for 30–40 minutes; the clot was outlined by a needle, then it was put into a refrigerator for 1 hour+4° C. After cooling it was centrifuged at 3000 RPM during 10–15 minutes. Serum with no signs of hemolysis was sampled into a clean tube. All quantitative indices of the blood biochemical characteristics were obtained by spectrophotometric measurements. Calibration curves to determine total protein and cholesterol were constructed in advance.

As shown in Table 8, 30 minutes after injection of S-ethylisothiouronium diethylphosphate at a dose of 500 mg/kg an increase in the concentration of total protein, cholesterol and glucose was observed, which subsequently had the tendency for normalization.

In the chronic experiment (at the dose of 100 mg/kg) it was shown that fluctuations of the studied parameters do not exceed the limits of physiological fluctuations and do not cause observed changes in biochemical indices (Table 9).

In an experiment on dogs, the functional condition of the organism was estimated by biochemical tests, after the intravenous injection of a 10% solution S-ethylisothiouronium diethylphosphate, at a dose of 10 mg/kg daily. This experiment was conducted at the same time of the day. Blood was examined 1 hour after the administration of the preparation during 3 successive days and on the 4th, the 5th and on the 10th day after injection. The concentrations of total protein, of albumin, globulins, total cholesterol, and glucose in dog blood serum were determined by conventional methods. The total protein content was determined by biureth method, total cholesterol—by like method, glucose—by glucose-oxidase method. The results are summarized in Tables 10–14.

TABLE 10

Influence of a daily intravenous injection of S-ethylisothiouronium diethylphosphate (3 × 10 mg/kg) on the concentration of total protein of dog blood serum

|  |  |  |  | 1st day | | 2nd day | | 3d day | | 4th day | | 5th day | | 10th day | |
|---|---|---|---|---|---|---|---|---|---|---|---|---|---|---|---|
| Dog # | Mass | Age | Sex | Before inject. | After inject. | Before inject. | After inject. | Before inject. | After inject. | Before inject. | After inject. | Before inject. | After inject. | Before inject. | After inject. |
| 820 | 18.2 | 1 | m | 49.6 | 63.4 | 63.4 | 55.2 | 55.2 | 63.4 |  | 46.8 |  |  |  |  |
| 833 | 21.0 | 3 | f | 63.4 | 52.4 | 62.0 |  |  | 49.6 |  | 38.6 |  |  |  |  |
| 735 | 22.0 | 3 | f | 55.2 | 53.8 | 55.2 | 63.4 | 60.6 | 52.4 |  |  |  | 23.4 |  |  |
| 864 | 18.5 | 2 | f | 49.6 | 57.9 | 74.4 |  |  |  |  |  |  |  |  | 75.8 |
| 892 | 19.0 | 2 | m | 88.2 |  | 85.5 | 60.6 | 82.7 | 46.9 |  |  |  | 48.2 |  |  |

TABLE 11

Influence of a daily intravenous injection of S-ethylisothiouronium diethylphosphate (3 × 10 mg/kg) on the albumin content (g/l) of dog blood serum

|  |  |  |  | 1st day | | 2nd day | | 3d day | | 4th day | | 5th day | | 10th day | |
|---|---|---|---|---|---|---|---|---|---|---|---|---|---|---|---|
| Dog # | Mass | Age | Sex | Before inject. | After inject. | Before inject. | After inject. | Before inject. | After inject. | Before inject. | After inject. | Before inject. | After inject. | Before inject. | After inject. |
| 820 | 18.2 | 1 | m |  | 20.0 |  | 20.0 | 26.6 | 25.0 |  |  |  |  |  |  |
| 833 | 21.0 | 3 | f | 29.1 |  | 23.3 |  |  | 31.6 |  | 21.6 |  |  |  |  |
| 735 | 22.0 | 3 | f | 35.0 | 28.3 | 25.0 | 30.0 | 33.3 | 33.3 |  |  |  | 13.8 |  |  |

TABLE 11-continued

Influence of a daily intravenous injection of S-ethylisothiouronium diethylphosphate (3 × 10 mg/kg) on the albumin content (g/l) of dog blood serum

| Dog # | Mass | Age | Sex | 1st day Before inject. | 1st day After inject. | 2nd day Before inject. | 2nd day After inject. | 3d day Before inject. | 3d day After inject. | 4th day Before inject. | 4th day After inject. | 5th day Before inject. | 5th day After inject. | 10th day Before inject. | 10th day After inject. |
|---|---|---|---|---|---|---|---|---|---|---|---|---|---|---|---|
| 864 | 18.5 | 2 | f | 20.8[1] | | 36.6 | 28.3 | | | | | | | | 21.6 |
| 892 | 19.0 | 2 | m | 20.0 | | 25.0 | 48.3 | 35.0 | 31.7 | | | | 18.3 | | |

TABLE 12

Influence of a daily intravenous injection of S-ethylisothiouronium diethylphosphate (3 × 10 mg/kg) on the globulin content (g/l) of dog blood serum

| Dog # | Mass | Age | Sex | 1st day Before inject. | 1st day After inject. | 2nd day Before inject. | 2nd day After inject. | 3d day Before inject. | 3d day After inject. | 4th day Before inject. | 4th day After inject. | 5th day Before inject. | 5th day After inject. | 10th day Before inject. | 10th day After inject. |
|---|---|---|---|---|---|---|---|---|---|---|---|---|---|---|---|
| 820 | 18.2 | 1 | m | | 43.4 | | 35.2 | | 25.0 | | | | | | |
| 833 | 21.0 | 3 | f | 39.2 | | 29.1 | | | 29.0 | | | 17.0 | | | |
| 735 | 22.0 | 3 | f | 20.2 | 25.5 | 30.2 | 33.4 | 27.3 | 19.1 | | | | 15.8 | | |
| 864 | 18.5 | 2 | f | 28.8 | | 37.8 | 26.9 | | | | | | | | 54.2 |
| 892 | 19.0 | 2 | m | 14.9 | 34.3 | 60.5 | 12.3 | 47.7 | 15.2 | | | | 29.9 | | |

TABLE 13

Influence of a daily intravenous injection of S-ethylisothiouronium diethylphosphate (3 × 10 mg/kg) on the total cholestrol content (mmol/l) of dog blood serum

| Dog # | Mass | Age | Sex | 1st day Before inject. | 1st day After inject. | 2nd day Before inject. | 2nd day After inject. | 3d day Before inject. | 3d day After inject. | 4th day Before inject. | 4th day After inject. | 5th day Before inject. | 5th day After inject. | 10th day Before inject. | 10th day After inject. |
|---|---|---|---|---|---|---|---|---|---|---|---|---|---|---|---|
| 820 | 18.2 | 1 | m | 6.2 | 6.2 | 6.0 | 6.4 | 9.0 | 8.4 | | | | | | |
| 833 | 21.0 | 3 | f | 8.8 | 7.2 | 6.4 | 7.2 | 8.8 | 9.6 | | | 6.0 | | | |
| 735 | 22.0 | 3 | f | 5.8 | 6.6 | 6.6 | 6.4 | 6.8 | 6.4 | | | | 7.2 | | |
| 864 | 18.5 | 2 | f | 6.2 | 6.6 | 8.0 | 6.0 | | | | | | | | 8.8 |
| 892 | 19.0 | 2 | m | 8.4 | 6.2 | 6.2 | 8.2 | 6.3 | 8.0 | | | | 6.2 | | |

TABLE 14

Influence of a daily intravenous injection of S-ethylisothiouronium diethylphosphate (3 × 10 mg/kg) on the glucose content (mmol/l) of dog blood serum

| Dog # | Mass | Age | Sex | 1st day Before inject. | 1st day After inject. | 2nd day Before inject. | 2nd day After inject. | 3d day Before inject. | 3d day After inject. | 4th day Before inject. | 4th day After inject. | 5th day Before inject. | 5th day After inject. | 10th day Before inject. | 10th day After inject. |
|---|---|---|---|---|---|---|---|---|---|---|---|---|---|---|---|
| 820 | 18.2 | 1 | m | 2.03 | 5.17 | 1.84 | 2.03 | 1.84 | 2.40 | | | 5.90 | | | |
| 833 | 21.0 | 3 | f | 6.10 | 3.89 | 4.25 | | 5.00 | 31.6 | | | 5.0 | | | |
| 735 | 22.0 | 3 | f | 1.84 | 1.84 | 1.92 | 1.70 | 1.70 | 2.40 | | | | 3.70 | | |
| 864 | 18.5 | 2 | f | 2.40 | 2.03 | 3.33 | | | 6.28 | | | | | | 7.77 |
| 892 | 19.0 | 2 | m | 5.36 | 6.66 | 4.07 | 5.92 | 6.66 | 5.36 | | | | 4.07 | | |

The level of total protein after introduction of the preparation had wavy fluctuations with the tendency to decrease on the 4th and 5th day. The level of albumins and globulins also changed in a wavy manner. The level of total cholesterol and glucose had slight fluctuations which did not overstep the fluctuation limits of healthy dogs.

The general toxicity and biochemical parameters were determined in a 3-day experiment, where a 10% solution of the preparation was daily intravenously injectioned at a dose of 10 mg/kg. Based on the results of the above experiments, it is possible to conclude that the preparation has no significant effect on the health of dogs; no evidence was found for intoxication or any significant deviation between the parameters studied and the initial data; individual sensitivity of the animals to intravenous injection of the preparation was not found.

As a result of the pathomorphological examination of internal organs of the animals (mice, dogs) which were exposed to S-ethylisothiouronium diethylphosphate in mean lethal and sublethal doses, it is concluded that this preparation causes moderately pronounced signs of hemodynamic disturbance in the form of gap widening and plethora primarily in small and medium vessels of the arterial and venous bed, mainly in the liver, miocard, lungs, spleen, and to a lesser extend in kidneys on the early stages. The disturbance to blood circulation has a reversible character and as a rule, it normalized within 7–10 days after the preparation had no longer any effect. No prounced inflammatory, distrophic or necrobiotic changes of internal organs were observed in these experiments. In some cases, signs of compensatory-adaptation reactions of liver (Kupfer cell proliferation, hyperchromia of cytoplasm hepatocyte nuclei) were noted.

C. Biological study of the oxygen protective activity of S-ethylisothiouronium diethylphosphate (Difetur) compared to that of Etyron Animals were exposed to oxygen under increased pressure in a hyperbaric chamber <<Mana-2≦≦ for treatment of infants above 1 year, which was adjusted for the experiments on animals. The hyperbaric chamber design permitted to create excessive pressure up to 3 atm and to observe animal behavior from outside.

The experiments were performed on males of $F_1$(CBAx57B1) mice line and on males of Wistar rat line. Animals were placed in the hyperbaric chamber in plastic boxes and the atmospheric air was replaced by oxygen. The period of compression-decompression was 10 minutes. The exposure of the animals to an oxygen pressure of 3 atm during a period of 2 hours caused only some increase in their motion activity. Further staying of rats and mice in those conditions led to a decrease in the motion activity, to asphyxia with short periods of excitement and cramps. The death of some animals was registered after 2.5–3 hours, 50% after 4 hours, and 75% of mice and 100% of rats were dead after 5 hours.

When the influence of Difetur and Etyron was studied, the animals were exposed to an oxygen pressure of 3 atm during 5 hours if not otherwise specified. Preparations were injected 5–10 minutes before the session. The results of this study are shown in Table 15.

After the session the dead animals were autopsied, their lungs were removed, and the index <<lung mass in gr./body mass in gr. X100>> (i.e. lung coefficient) was defined.

The hyperbaric conditions lead to the increase of lung coefficient up to 1.43±0.08 in mice and up to 1.45±0.08 in rats. Preliminary injection of Difetur at doses of 5, 10, and 20 mg/kg cause to a decrease in the lung coefficients to 0.95±0.09, 0.97±0.09 and 0.88±0.08 respectively. Thus, Difetur presents a considerable protective efficiency regarding the lung tissue.

Experiments on the toxic effect of oxygen at a pressure of 6 atm were carried out similarly in a hyperbaric chamber C-203 (chamber volume 0.45 m$^3$), on white rats, during 50 minutes. The preparation was injected intraperitoneally at a dose of 20 mg/kg. In the controls, 2 ml/kg of water for injections was injected intraperitoneally. After decompression the rats were decapitated and the glucose content, urea content, ureal nitrogen and total hemoglobine content were determined in the blood serum, as well as the index <<lung mass in gr./body mass in gr. X 100>> (i.e. lung coefficient). The results are summarized in Tables 16 to 18.

Table No. 16 shows that an oxygen pressure of 6 atm caused cramps in 90.5% of the cases; terminal state (lateral position) - in 40.1% of the cases; in 53.7% - asphyxia and in 26.9% - death of the animals. The oxygen poisoning was accompanied by increase in the levels of glucose, hemoglobin, ureal nitrogen and urea in the blood serum. S-ethylisothiouronium diethylphosphate (Difetur) did not practically effect the hemoglobin content but considerably improved other indices. This preparation significantly reduced the <<lung mass in gr./body mass>> index in comparison with that of untreated animals. It should be noted that Difetur completely prevented animals' death and reduced other visible consequences of the oxygen poisoning.

TABLE 15

The influence of S-ethylisothiouronium diethylphosphate (Difetur) and Etyron on animals exposed to an oxygen pressure of 3 atm.

| | Number of survived animals, % | | |
|---|---|---|---|
| Preparation | 5 mg/kg | 10 mg/kg | 20 mg/kg |
| Mice experiments | | | |
| Etyron | — | 70 | 50 |
| Preparation | 25 | 65 | 88 |
| Control 25 | | | |
| Rat experiments | | | |
| Preparation | 60 | 50 | 70 |
| Control 0 | | | |

TABLE 16

The influence of S-ethylisothiouronium diethylphosphate and Etyron on rats exposed to an oxygen pressure of 6 atm.

| Experiment conditions | Animal number | Animal number Generalized cramps | Asphyxia | Lateral position | Number of perished rats |
|---|---|---|---|---|---|
| Control | 568 | 514 (90.5%) | 305 (53.7%) | 228 (40.1%) | 153 (26.9%) |
| Preparation | 36 | 1 (2.8%) | 0 | 0 | 0 |

TABLE 17

The influence of S-ethylisothiouronium diethylphosphate on the blood serum biochemical indices

| | Glucose | | Hemoglobin | | Urea | | Urea Nitrogen | |
|---|---|---|---|---|---|---|---|---|
| Experiment conditions | n | M ± m | n | M ± m | n | M ± m | n | M ± m |
| Preparation | 16 | 5.765 ± 0.214 | 16 | 2.028 ± 0.048 | 16 | 4.643 ± 0.212 | 16 | 2.163 ± 0.099 |
| Controls under 6 atm pressure | 13 | 10.056 ± 0.726 | 17 | 2.002 ± 0.057 | 13 | 5.698 ± 0.218 | 13 | 2.642 ± 0.104 |
| Controls under regular conditions | 16 | 5.443 ± 0.110 | 18 | 1.692 ± 0.039 | 16 | 4.934 ± 0.214 | 16 | 2.299 ± 0.099 |

TABLE 18

The influence of S-ethylisothiouronium diethylphosphate on the <<lung mass in gr./body mass in gr. X 100>> index (i.e. lung coefficient)

| Experiment conditions | Number of animals | Average ± S D |
|---|---|---|
| Preparation | 16 | 0.474 ± 0.024 |
| Controls under oxygen pressure of 6 atm | 20 | 0.975 ± 0.094 |
| Controls in ordinary conditions | 21 | 0.609 ± 0.140 |

D. Clinical testing (in vivo) of S-ethylisothiouronium diethylphosphate (Difetur)

This experiment was conducted at the General Anesthesia Department of the First Republican Hospital of Moldova. The goal of this clinical study was to estimate the ability of Difetur to act as a hypertensive drug, compared to the known adrenergic drug—ephedrine. The experiments were performed on one hundred patients, underwent urological operations under spinal epidural anesthesia, their age being between 20 and 80. The following findings are presented in view of Difetur:

1. Administration of Difetur prior to the epidural anesthesia prevented the decrease in the patient's blood pressure. Its administration was best accomplished when it was introduced slowly by infusion.
2. The hypertensive action of Difetur persists for 40–60 minutes. The blood pressure attains the initial value within 90 minutes.
3. No cases of secondary hypertension were observed.
4. No complications of allergic type of the blood circulation or respiration were observed.
5. The blood pressure of the patients remained stable after administration of Difetur.

In view of the above results, it is estimated that Difetur (S-ethylisothiouronium diethylphosphate) is a potential hypertensive drug, which has a rapid and prolonged effect on arterial blood pressure. When it is provided prior to epidural anesthesia, Difetur improves and corrects impairment in blood circulation.

What is claimed is:

1. A method of increasing arterial blood pressure, comprising administering to a mammal in need of such treatment a therapeutically effective amount of a compound of formula I:

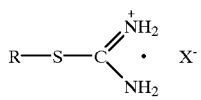

I wherein R is a straight or branched alkyl, optionally substituted by halogen and X is an anion derived from a phosphorus containing acid.

2. A method to alleviate the symptoms of disorders associated with low blood pressure, comprising administering to a mammal in need of such treatment a therapeutically effective amount of a compound of formula I given in claim 1.

3. A method according to claim 1, for treating a disease or disorder selected from the group consisting of acute arterial hypotonia due to surgical interference, trauma or poisoning, oxygen poisoning, shock condition, hemorrhage, hypotonia as resulted from epidural anesthesia and in conditions where adrenomimetics are counter-indicated or ineffective.

4. A method according to claim 1, wherein the compound of formula I is selected from the group consisting of:

S-methylisothiouronium methylphosphite;
S-methylisothiouronium dimethylphosphite;
S-ethylisothiouronium metaphosphite;
S-ethylisothiouronium ethylphosphite;
S-ethylisothiouronium diethylphosphate;
S-propylisothiouronium propylphosphite;
S-isopropylisothiouronium methylphosphate;
S-isopropylisothiouronium isopropylphosphite;
S-butylisothiouronium dibutylphosphate; and
S-isobutylisothiouronium isobutylphosphite.

5. A method according to claim 1, wherein the active compound is administered at a dose of between 0.1 mg/kg and about 20 mg/kg.

6. The method according to claim 1, wherein the compound of formula I is S-ethylisothiouronium diethylphosphate.

7. The method according to claim 1, in the case of an emergency, wherein the compound is administered in the form of an injectable medicament containing about 1–10% of said compound.

8. The method according to claim 1, wherein said compound is administered in the form of a tablet or capsule.

9. A method for protection of organs or tissues from damages which may result from hyperoxic conditions, comprising administering to a mammal in need of such treatment a therapeutically effective amount of a compound of formula I:

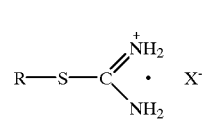

I wherein R is a straight or branched alkyl, optionally substituted by halogen and X is an anion derived from a phosphorus containing acid.

10. The method according to claim 9, wherein the compound of formula I is S-ethylisothiouronium diethylphosphate.

11. The method according to claim 9, in the case of an emergency, wherein the compound is administered in the form of an injectable medicament containing about 1–10% of said compound.

12. The method according to claim 9, wherein said compound is administered in the form of a table or capsule.

13. A method according to claim 9, wherein the compound of formula I is selected from the group consisting of:

S-methylisothiouronium methylphosphite;
S-methylisothiouronium dimethylphosphate;
S-ethylisothiouronium metaphosphate;
S-ethylisothiouronium ethylphosphite;
S-ethylisothiouronium diethylphosphate;
S-propylisothiouronium propylphosphite;
S-isopropylisothiouronium methylphosphate;
S-isopropylisothiouronium isopropylphosphite;
S-butylisothiouronium dibutylphosphate; and
S-isobutylisothiouronium isobutylphosphite.

14. A method according to claim 9, wherein the active compound is administered at a dose of between 0.1 mg/kg and about 20 mg/kg.

* * * * *